(12) United States Patent
Fisker et al.

(10) Patent No.: US 9,872,745 B2
(45) Date of Patent: Jan. 23, 2018

(54) MODELING A DIGITAL DESIGN OF A DENTURE

(71) Applicant: 3Shape A/S, Copenhagen K (DK)

(72) Inventors: Rune Fisker, Virum (DK); Morten Ryde Hansen, Asnaes (DK)

(73) Assignee: 3Shape A/S, Copenhagen K (DK)

( * ) Notice: Subject to any disclaimer, the term of this patent is extended or adjusted under 35 U.S.C. 154(b) by 394 days.

(21) Appl. No.: 14/378,178

(22) PCT Filed: Feb. 14, 2013

(86) PCT No.: PCT/EP2013/052990
§ 371 (c)(1),
(2) Date: Aug. 12, 2014

(87) PCT Pub. No.: WO2013/120955
PCT Pub. Date: Aug. 22, 2013

(65) Prior Publication Data
US 2015/0111177 A1    Apr. 23, 2015

Related U.S. Application Data

(60) Provisional application No. 61/598,597, filed on Feb. 14, 2012, provisional application No. 61/701,055, filed on Sep. 14, 2012.

(30) Foreign Application Priority Data

Feb. 14, 2012  (DK) .................................. 2012 00121
Sep. 14, 2012  (DK) .................................. 2012 70566

(51) Int. Cl.
*A61C 13/01*    (2006.01)
*A61C 13/00*    (2006.01)
(Continued)

(52) U.S. Cl.
CPC .............. *A61C 13/01* (2013.01); *A61C 9/004* (2013.01); *A61C 13/0004* (2013.01);
(Continued)

(58) Field of Classification Search
CPC . A61C 13/0001; A61C 13/0004; A61C 13/34; A61C 13/08; A61C 9/0053; A61C 19/045; A61C 19/05
(Continued)

(56) References Cited

U.S. PATENT DOCUMENTS 8,422,751 B2 *  4/2013  Kim ..................... G05B 19/401
                                                    250/559.01
8,425,229 B2 *  4/2013  Nilsson ............... G06F 19/3437
                                                    433/172
(Continued)

FOREIGN PATENT DOCUMENTS

EP       2 026 285 A1    2/2009
WO   WO 2008/005432 A2   1/2008
(Continued)

OTHER PUBLICATIONS

International Search Report (PCT/ISA/210) dated Jun. 6, 2013, by the European Patent Office as the International Searching Authority for International Application No. PCT/EP2013/052990.
(Continued)

*Primary Examiner* — Nicholas Lucchesi
(74) *Attorney, Agent, or Firm* — Buchanan Ingersoll & Rooney PC

(57) ABSTRACT

Disclosed is a method for modeling a digital design of a denture for a patient, said denture comprising a gingival part and a teeth part comprising a set of denture teeth, where the method comprises:
  obtaining a digital 3D representation of the patient's gum;
  obtaining virtual teeth models corresponding to the denture teeth;
(Continued)

virtually arranging the virtual teeth models in relation to the digital 3D representation of the patient's gum; and generating a virtual outer gingival surface of the gingival part of the denture.

25 Claims, 26 Drawing Sheets

(51) Int. Cl.
  *A61C 13/08*    (2006.01)
  *A61C 9/00*    (2006.01)
  *A61C 19/045*    (2006.01)
  *A61C 19/05*    (2006.01)

(52) U.S. Cl.
  CPC ............ *A61C 13/08* (2013.01); *A61C 9/0053* (2013.01); *A61C 19/045* (2013.01); *A61C 19/05* (2013.01)

(58) Field of Classification Search
  USPC .................................. 433/196, 213, 214, 223
  See application file for complete search history.

(56) References Cited

U.S. PATENT DOCUMENTS

| | | | |
|---|---|---|---|
| 8,651,858 B2* | 2/2014 | Berckmans, III | A61C 1/084 433/24 |
| 9,295,534 B2* | 3/2016 | Ruppert | A61C 13/0004 |
| 2002/0094509 A1* | 7/2002 | Durbin | A61C 9/00 433/213 |
| 2004/0175671 A1 | 9/2004 | Jones et al. | |
| 2005/0019732 A1* | 1/2005 | Kaufmann | A61C 7/00 433/213 |
| 2006/0040236 A1* | 2/2006 | Schmitt | A61C 13/0004 433/213 |
| 2007/0190492 A1 | 8/2007 | Schmitt | |
| 2007/0190493 A1 | 8/2007 | Yamamoto et al. | |
| 2007/0287131 A1* | 12/2007 | Ruppert | A61C 13/0004 433/223 |
| 2009/0287332 A1 | 11/2009 | Adusumilli et al. | |
| 2012/0015330 A1 | 1/2012 | Zhivago | |
| 2012/0072178 A1 | 3/2012 | Beaudry et al. | |
| 2014/0032183 A1* | 1/2014 | Fisker | A61C 13/0004 703/1 |
| 2014/0051037 A1* | 2/2014 | Fisker | A61C 8/0048 433/213 |
| 2015/0132718 A1* | 5/2015 | Kerschensteiner | A61C 13/01 433/196 |

FOREIGN PATENT DOCUMENTS

| | | |
|---|---|---|
| WO | WO 2011/077175 A1 | 6/2011 |
| WO | WO 2011/103876 A1 | 9/2011 |
| WO | WO 2012/000511 A1 | 1/2012 |
| WO | WO 2012/041329 A1 | 4/2012 |

OTHER PUBLICATIONS

Danish Search Report dated Sep. 7, 2012 for Danish Application No. PA 2012 00121.

* cited by examiner 1728
1732
1733

1728
1737
1764
1733

MODELING A DIGITAL DESIGN OF A DENTURE

This invention generally relates to a method for modeling a digital design of a denture. More particularly, the invention relates to a method for modeling the gingival part and/or the teeth part of the denture.

Disclosed is a method for modeling a digital design of a denture for a patient, said denture comprising a gingival part and a teeth part comprising a set of denture teeth, where the method comprises:
- obtaining a digital 3D representation of the patient's gum;
- obtaining virtual teeth models corresponding to the denture teeth;
- virtually arranging the virtual teeth models in relation to the digital 3D representation of the patient's gum; and
- generating a virtual outer gingival surface of the gingival part of the denture.

Disclosed is a computer program product comprising program code means for causing a data processing system to perform the method of the present invention, when said program code means are executed on the data processing system.

In some embodiments, the computer program product comprises a computer-readable medium having stored there on the program code means.

Disclosed is a non-transitory computer readable medium storing thereon a computer program, where said computer program is configured for causing computer-assisted modeling a digital design of a denture for a patient, said denture comprising a gingival part and a teeth part comprising a set of denture teeth, where the modeling comprises: obtaining a digital 3D representation of the patient's gum, obtaining virtual teeth models corresponding to the denture teeth, virtually arranging the virtual teeth models in relation to the digital 3D representation of the patient's gum, and generating a virtual outer gingival surface of the gingival part of the denture.

Disclosed is a data processing system for modeling a digital design of a denture for a patient, said denture comprising a gingival part and a teeth part comprising a set of denture teeth, where the system comprises
- a data processing unit configured for obtaining a digital 3D representation of the patient's gum, and for obtaining virtual teeth models corresponding to the denture teeth; and
- a nontransitory computer readable medium having one or more computer instructions stored thereon, where said computer instructions comprises instructions for virtually arranging the virtual teeth models in relation to the digital 3D representation of the patient's gum, and for generating a virtual outer gingival surface of the gingival part of the denture when said instructions are executed on said data processing unit.

Disclosed is a system for modeling a digital design of a denture for a patient, said denture comprising a gingival part and a teeth part comprising a set of denture teeth, where the system comprises
- a scanner unit configured for obtaining a digital 3D representation of the patient's gum,
- a unit configured for obtaining virtual teeth models corresponding to the denture teeth; and
- a nontransitory computer readable medium having one or more computer instructions stored thereon, where said computer instructions comprises instructions for virtually arranging the virtual teeth models in relation to the digital 3D representation of the patient's gum, and generating a virtual outer gingival surface of the gingival part of the denture.

According to an aspect of the invention is a method for modeling a digital design of a denture for a patient, said denture comprising a gingival part and a teeth part comprising a set of denture teeth, where the method comprises:
- obtaining a digital 3D representation of the patient's gum;
- obtaining virtual teeth models corresponding to the denture teeth;
- virtually arranging the virtual teeth models in relation to the digital 3D representation of the patient's gum; and
- generating a virtual outer gingival surface of the gingival part of the denture.

Disclosed is a method for manufacturing a denture for a patient, where the denture comprises a gingival part and denture teeth, wherein the method comprises:
- obtaining a digital denture design, where the digital denture design is modeled using the method according to the present invention;
- manufacturing at least part of the denture by means of computer aided manufacturing (CAM).

When the virtual teeth models have been virtually arranged in relation to the digital 3D representation of the patient's gum, the virtual outer gingival surface of the gingival part of the denture can be generated using a number of computer implemented techniques, such as by a loofting process or by copying or modifying appropriate surfaces of the digital 3D representation of the patient's gums.

It is an object of the present invention to provide a method for digitally designing a denture by virtually arranging the denture teeth and virtually generating the gingival part of the denture such that a denture manufactured from the digital design has a pleasant appearance and feel.

The outer gingival surface of a manufactured denture is visible when the denture is arranged in the patient's mount.

It is an object of the present invention to provide that the generated virtual outer gingival surface is such that a denture manufactured from the digital denture design has an aesthetically pleasant and natural look.

It is an object of the present invention to provide that the generated virtual outer gingival surface is such that a denture manufactured from the digital denture design is shaped such that the outer gingival surface causes minimum discomfort to the patient when wearing the denture.

The gingival part of the denture comprises an inner gingival surface which faces or contacts surfaces of the patient's oral cavity when the denture is arranged in the patient's mouth. Preferably, the digital design of the denture also comprises a corresponding virtual inner gingival surface.

In some embodiments, the method comprises generating the virtual inner gingival surface.

It is an object of the present invention to provide that the inner gingival surface of a manufactured from the digital denture design causes minimum discomfort to the patient when wearing the denture.

In some embodiments, the virtual outer gingival surface and the virtual outer gingival surface are generated concurrently In some embodiments the obtained digital 3D representation of the patient's gum relates to the patient's upper jaw, to the patient's lower jaw, or to both.

In some embodiments, the part of the patient's gum(s) that is scanned when obtaining the digital 3D representation comprises one or more healthy teeth, such as when the digital design is of a partial denture.

When designing a denture for one of the patient's jaws it may also be relevant to scan antagonist jaw even though no denture is needed for this jaw. When the digital 3D representation of the patient's gums comprises the antagonist jaw and associated teeth the design of the denture can take into account the occlusion of the teeth.

In some embodiments, a part of the virtual outer gingival surface is formed by copying or transferring the corresponding part of the obtained digital 3D representation. This provides the advantage that the gingival part of a denture manufactured from the digitally designed denture will have an outer surface which resembles the natural surface of the oral cavity such that the denture will have a more pleasant and natural look. Wearing the denture will also cause less discomfort to the patient when e.g. the palette part of the denture resembles the patient's own palette.

In some embodiments, the part of the patient's gum(s) that are scanned when obtaining the digital 3D representation relates to at least the alveolar ridge and/or the palette at which the denture is to be arranged such that the obtained digital 3D representation of the gums comprises data relating to the alveolar ridge and/or to the palette.

In some embodiments, the alveolar ridge and/or the palette of the obtained digital 3D representation is used in the design of the denture, such as used when generating the virtual outer gingival surface of the gingival part of the denture. For example, the virtual outer surface of the gingival part of the denture at the alveolar ridge can then be designed to resemble the corresponding surfaces of the patient's alveolar ridge, such that the manufactured denture will appear more natural.

It may be advantageous that the designing of the denture comprises copying/transferring the shape of the patient's own palette area from the digital 3D representation of the patient's gums to the denture design, since this can improve the fit of the denture. Further it allows for a design of the denture in which the palette part of the virtual outer gingival surface is shaped according to the patient's natural palette.

In some embodiments, a surface of the denture configured for contacting or facing a section of the patient's gums is designed by copying or transferring the part of the digital 3D representation of the patient's gums corresponding to this section.

This may have the advantage that the patient may feel less discomfort when have the denture arranged the mouth.

The virtual outer gingival surface of the gingival part of the denture can be generated concurrently with the virtual gingiva surface configured for facing or contacting the appropriate surface of the patient's oral cavity.

In the context of the present invention, the occlusal plane may be represented by the following three points on a dentulous jaw: the contact point of the incisal edges of the lower central incisors (incisal point), and the tips of the distobuccal cusps of the second lower molars. This is mostly situated at the height of the lip closure line.

In the context of the present invention, the phrase "digital design of a denture" is used interchangeably with the phrase "digital denture design".

In the context of the present invention, the phrase "mandibular occlusion rim" is used interchangeably with the phrase "lower wax rim"

In the context of the present invention, the phrase "maxillary occlusion rim" is used interchangeably with the phrase "upper wax rim"

In the context of the present invention, the phrase "wax rim" is used interchangeably with the phrase "Wax Occlusal Rim model".

Several steps of the method can be computer implemented such that digital precision and efficiency can be applied to a traditionally technique demanding process. The invention provides that technicians can model highly esthetic and functional dentures while significantly shortening the design step.

The denture design workflow may comprise setting occlusion, modeling gingiva design, placing teeth, and making fine adjustments such as bite height and more. With a computer implementation of the method the operator may use computer implemented free-form sculpt tools and dynamic virtual articulation in modeling the digital design of the denture and make all the necessary adjustments for optimal occlusion, esthetics and functionality.

The teeth part of the denture may be based on fixed size pre-manufactured acrylic teeth or on customized individual teeth made e.g. using CAD/CAM technology.

The invention provides that the operator quickly can adjust all teeth, upper and lower as well as left and right sides simultaneously, while preserving the correct bite. Using virtual occlusal plates the combined occlusion can easily be updated. A virtual articulation can then be applied to optimize the denture's dynamic occlusion.

The occlusion can be established in different ways depending on the case, or preferred workflow.

In some embodiments, a Wax Occlusal Rim model is scanned to define relative upper and lower position and the patient's occlusal plane.

In some embodiments, the upper/lower wax rim models are scanned separately and virtually brought into occlusion using flexible adjustment tools.

In some embodiments the method comprises obtaining the patient's occlusal plane by means of a facebow.

In some embodiments the facebow is an electronic facebow.

The electronic facebow may output different patient specific parameters which can be used for setting a virtual articulator, for example as described in 3Shape's patent applications WO2011/103876 and DK/PA 2012 70138.

In some embodiments the facebow is a mechanical facebow.

After setting and adjusting the mechanical facebow for the patient's face, the facebow can be arranged in a mechanical articulator, and the positions from the articulator can be transferred to a virtual articulator by means of for example transfer plates, adapter plates, male and female plates etc, as described in 3Shape's patent applications WO2011/103876 and DK/PA 2012 70138.

In some embodiments the method comprises obtaining the patient's occlusal plane by means of physical impressions of the patient's upper and lower gums and/or by one or more measurements of the patient's face and mouth.

The physical impressions may be obtained by using a tray filled with e.g. border moulding material and/or impression material.

The tray may be a custom dental impression tray, such as described in 3Shape's patent application PCT/EP2012/062684.

The tray may be made of a thermoplastic material.

In some embodiments the method comprises:
  obtaining a 3D digital representation of the physical impression of the patient's upper jaw;
  obtaining a 3D digital representation of the physical impression of the patient's lower jaw; and
  obtaining a 3D digital representation of the physical impressions of the patient's upper jaw and lower jaw arranged together.

In some embodiments the patient's upper jaw and lower jaw are arranged together in occlusion.

It is an advantage to obtain a 3D digital representation of the combined physical impressions of the upper and lower jaw, since this may indicate their correct relative positions, whereby the denture can be designed properly.

In some embodiments the method comprises performing measurements of the patient's face and mouth.

The dentist may perform the measurements by means of different measurement devices. The measurement device can for example be a component which is fixed to the patient's gum and/or lips. The component may be fixed using e.g. impression material, bite registration material, biocompatible glue etc.

The measurements can be of the correct vertical height of the denture, the centric relation, lip support, bite plane, midline, smile line, central incisal line etc.

The occlusal plane may be obtained by a combination of using a facebow, performing measurements of the patient's face and mouth, obtaining physical impressions and/or obtaining wax rims.

In some embodiments the method comprises providing a straight occlusal plate.

In some embodiments the method comprises providing a curved occlusal plate.

The virtual occlusal plates can be curved, bended, flat, straight etc. The simplest type of occlusal plate may be a flat plate. However, often a patient's bite is not characterized by a completely flat bite or occlusion, and then a curved occlusal plate may be used.

The sagittal curve of the patient's mouth may determine the curvature of the occlusal plate.

The sagittal curve may be derived from the patient by moving models of the patient's lower and upper jaw relative to each other in a mechanical articulator and using the pin from a facebow to mark the movements in silicone material arranged under the pin. Then the movements performed in the silicone material can be recorded and the same movements can be performed either in a physical articulator or in a virtual articulator, as described in 3Shape's patent applications U.S. 61/664,343 and DK PA 2012 70371. This may be performed if the patient still has teeth in this/her mouth. If the patient has no teeth left, then a standard plate may be used for the movement.

In some embodiments the method comprises selecting a virtual occlusal plate for modeling the patient's denture.

In some embodiments the method comprises providing a virtual occlusal plate relative to digital 3D representations of the wax rims and/or the digital 3D representation of the patient's gums, and virtually arranging the virtual teeth models relative to the virtual occlusal plate.

This may provide that the virtual teeth models easily and quickly can be virtually arranged relative to each other and/or relative to the digital 3D representation of the patient's gum, i.e. relative to the gingival part of the denture.

In some embodiments the virtual teeth models in the lower jaw or the upper jaw are arranged in occlusion by means of a virtual occlusal plate, and the virtual teeth models are then arranged in the upper jaw or lower jaw, respectively, relative to the already arranged teeth models in the antagonist jaw.

If for example the patient has been missing his/her teeth for a long time, for example if the person is an older person, then the upper arch will have shrunken and the lower arch will have expanded, and the lower arch is therefore the dominant arch, and the teeth will first be arranged on the lower jaw, and then afterwards the teeth will be arranged in the upper jaw relative to the teeth in the lower jaw.

If for example the patient is a younger person who has only recently lost his/her teeth, then the upper jaw has not started shrinking yet, and the lower jaw has not started expanding, and in this case the upper jaw is the dominant jaw or arch, and the teeth will first be arranged on the upper jaw, and then afterwards the teeth will be arranged in the lower jaw relative to the teeth in the upper jaw.

A virtual articulator may be used for testing and checking the occlusion.

Alternatively and/or additionally a suitable digital test, performed by means of an algorithm, can be used to design, test and/or check the occlusion.

In some embodiments the virtual teeth models are virtually snapped to the occlusal plate.

Virtually snapped means fixed, attached, maintained, fastened, kept in virtual contact with the occlusal plate etc. Thus even though the operator adjusts the position, orientation and/or shape of the virtual teeth models the teeth models remains in the occlusion given by the occlusal plate.

In some embodiments the method comprises adjusting the curvature of the occlusal plate to provide that the occlusal plate substantially follows the curvature of the patient's jaws.

In some embodiments the method comprises adjusting the curvature of the occlusal plate by virtually pulling in one or more control points of the occlusal plate.

The control points may be pulled or dragged up, down, to the right side, to the left side etc. whereby the curvature of the occlusal plate is altered.

The occlusal plate may be straight by default, and the operator may then adjust the curvature of the occlusal plate relative to specific patient case.

In some embodiments the method comprises selecting virtual teeth models from a virtual library comprising virtual sets of teeth models, such as selecting a set of teeth models from a virtual library.

In some embodiments the different sets of teeth models from the virtual library have different arrangements of the teeth models, such as different arrangements of the teeth relative to each other.

In some embodiments the different sets of teeth models from the virtual library have different teeth shapes and/or sizes, such as round, square, triangular, short, long, wide and/or narrow.

In some embodiments a set of teeth models for the lower jaw and/or a set of teeth models for the upper jaw is/are selected.

In some embodiments the set of teeth models for the lower jaw and the set of teeth models for the upper jaw are a pair fitting together and arranged in occlusion.

Thus the shape of opposite teeth fit together, e.g. the cusps of the opposite posterior teeth in the lower and upper jaw match each other and fit in to each other.

In some embodiments the sets of teeth models in the library are provided by 3D scanning physical dentures comprising the physical versions of the teeth models arranged in the sets.

Thus the library sets may be obtained by building up dentures manually, scanning the dentures, where the artificial teeth are arranged in proper occlusion, and then saving this scan as a library teeth set up for denture.

In some embodiments the virtual teeth models are aligned relative to the sets of teeth models, such as where one or more virtual teeth models are aligned relative to the other teeth of the set of teeth models in which they are comprised and/or relative to the set of teeth models for the other jaw.

This provides that the virtual teeth models can be arranged very nicely relative to the digital 3D representation of the upper and/or lower jaw.

In some embodiments teeth models from different sets of teeth models are combined for the denture.

For example beautiful, esthetic teeth models for the anterior teeth are selected from a first set of teeth, and robust less esthetic teeth models are selected for the posterior teeth or molar teeth.

For example high teeth models are selected for the anterior teeth and low teeth models are selected for the posterior teeth, if the patient's mouth does not provide space enough in the back for high teeth.

In some embodiments the method comprises virtually adjusting the position, shape and/or orientation of one or more of the teeth models in the sets.

It is an advantage to adjust the position, shape and/or orientation of one or more of the teeth models for ensuring that the teeth models fits the patient and for ensuring that occlusion is obtained and/or maintained.

The software called Smile Composer from 3Shape may be used for adjusting the position, shape and/or orientation of the one or more teeth models.

In some embodiments virtually adjusting the position, shape and/or orientation of one or more of the teeth models in the sets comprises:
translating a tooth model;
rotating a tooth model; and/or
morphing a tooth model.

In some embodiments the occlusion of the set of teeth for the lower jaw and the set of teeth for the upper jaw is maintained, when the position, shape and/or orientation of one or more of the teeth models in the set(s) is adjusted.

In some embodiments the interproximal contact between neighbor teeth models is maintained, when the position, shape and/or orientation of one or more of the teeth models in the set(s) is adjusted.

In some embodiments the method comprises virtually adjusting the position, shape and/or orientation for a group of teeth models. The adjustment may be identical for all teeth in said group or it may scale with distance from a selected tooth in the group. The scaling may be such that the adjustment increases or decreases with the distance from the selected tooth.

In some embodiments the method comprises replacing one or more teeth models in the selected set of teeth with teeth models from another set of teeth from the library.

In some embodiments the method comprises virtually designing one or more of the teeth for the denture. The denture teeth can then be manufactured from the virtually designed teeth.

Thus instead of using pre-manufactured denture teeth, a dental designer may design one or more of the teeth for the denture from the beginning, and the designed teeth may then be manufactured, e.g. by rapid manufacturing methods, such as 3D printing, milling, sintering etc. Either all teeth for denture or only some teeth may be designed from the beginning.

In some embodiments the method comprises providing a number of characteristic points on the digital 3D representation of the lower jaw and/or on the digital 3D representation of the upper jaw In some embodiments, the characteristic points are used to determine the placement of teeth models on the jaw(s).

In some embodiments, the virtual set of teeth models selected from a virtual library of teeth models is selected based on the relative positions of the characteristic points.

In some embodiments providing the number of characteristic points comprises that an operator virtually places the characteristic points.

In some embodiments providing the number of characteristic points comprises that the characteristic points are automatically placed.

The characteristic points can be automatically placed or placed by the operator on the digital 3D representation of the jaw(s) based on certain rules for placement.

In some embodiments the characteristic points on the lower jaw comprise one or more of:
a retromolar pad #1;
a retromolar pad #2;
a first canine point;
a second canine point; and
a central ridge point.

In some embodiments the characteristic points on the upper jaw comprise one or more of:
tuberosity #1;
tuberosity #2;
a first canine point;
a second canine point; and
a central ridge point.

The tuberosities may be defined relative to or based on the distance between the canines.

The distance between the canines may furthermore define the size of the artificial denture teeth, such as the width of the teeth. Thus the set of teeth models from the library may be selected based on the distance between the canines.

Traditionally, the pre-manufactured teeth are arranged physically in wax by grinding away wax to make room for the pre-manufactured teeth. The teeth arranged in wax may be denoted a try-in, since the patient may try this in his/her mouth to check if it fits. If it does not fit well enough, the teeth can be adjusted in the wax. When the try-in fits the patient, the try-in can be placed in a mould where the wax can be melted away and acrylic can replace the wax around the pre-manufactured teeth.

According to the present method, in some embodiments a try-in denture is printed when the denture has been designed.

The patient can then try the printed try-in denture in his/her mouth to check if it fits. If it does not fit well enough, the teeth can be adjusted in the printed try-in, if the printed material allows for this.

In some embodiments a light-curable material is used for printing the try-in denture.

For example can a material which is light-curable be used, such that the printed material is ductile, moldable or formable before the light-curing such that the teeth can be adjusted in the gingival part. When the try-in denture fits the patient, the try-in can be light-cured to harden the material to ensure that the teeth stay in the position.

In some embodiments the printed try-in denture is 3D scanned after a potential adjustment of the teeth in the try-in denture.

It may be easy to register the adjusted teeth in the printed try-in denture, because the position and orientation of the teeth in the try-in denture are only adjusted slightly relative to their original position and orientation in the printed try-in denture.

In some embodiments a try-in denture is manufactured in wax, the wax try-in denture is 3D scanned, and based on the 3D scan of the wax try-in denture an acrylic final denture is printed.

Instead of producing a try-in denture, a digital test using a virtual articulator can be performed for testing whether the denture will fit the patient. If the digital 3D representation of the patient's gum is of good quality, and the virtual teeth models are arranged properly relative to the digital 3D representation of the teeth, then a try-in denture may not be required, and the digital test using a virtual articulator may be sufficient for ensuring that the denture fits the patient.

In some embodiments, the method comprises defining a gingival 3D spline marking an outer boundary curve of the denture directly on the digital 3D representation of the patient's gum or on the 3D scanned try-in denture when one of these are visualized on a computer screen. Based on the gingival 3D spline and the arrangement of the virtual teeth models, computer software can implement several steps of the method and automatically design the gingival part of the denture, such that it is perfectly shaped to fit the denture teeth. This can be done with limited effort by the operator. Anatomical details of the gingival part can be added with the operators own artistic touch using computer implemented virtual sculpt and edit tools.

When the modeling of the digital design of the denture designs is complete, the resulting virtual model of the denture is completely ready for efficient output on a variety of milling machines or 3D printers. The gingival part of the denture can be produced to match perfectly pre-manufactured acrylic teeth or custom manufactured teeth.

In some embodiments, the method comprises defining a gingival 3D spline in relation to the digital 3D representation of the patient's gum. The gingival 3D spline is configured for defining a gingival edge or boundary of the denture i.e. the circumference/outer boundary of the gingival part of the denture.

In computer implemented embodiments, the gingival 3D spline may be drawn directly on the digital 3D representation of the patient's gum on a computer screen.

The system of the invention may the automatically design the gingiva part of the denture and provide that it is perfectly shaped to fit the teeth.

In some embodiments the method comprises virtually arranging the virtual teeth models relative to the gingival part of the denture.

In some embodiments, part of the gingival 3D spline is arranged at the sulcus of the patient's gingival.

In some embodiments, part of the gingival 3D spline is arranged at the patient's ah-line.

In some embodiments, the virtual outer gingival surface is configured for connecting the gingival 3D spline and the virtual teeth models. I.e. the generated virtual outer gingival surface is shaped such that it is bounded at least in part by the gingival 3D spline and the surface of the virtual teeth models.

In some embodiments, gingival-tooth lines are defined for said virtual teeth models and said virtual outer gingival surface contacts said virtual teeth models at said gingival-tooth line.

This has the advantage that the look of the denture can be determined at least partly by the gingival-tooth line. In some cases the gingival-tooth line is predefined based on the structure of the denture tooth while in other cases an operator defines the gingival-tooth line. In both cases the shape of the virtual outer gingival surface at the denture can to some extent be automatically determined based on the defined gingival-tooth lines.

In some embodiments the method comprises connecting the virtual outer gingival surface to the gingival-tooth lines on the virtual teeth models.

In some embodiments the method comprises extending the virtual outer gingival surface into the interproximal gap between the teeth models.

It is an advantage that the outer gingival surface is extended past the gingival-tooth lines on the virtual teeth models at the gaps between teeth, since this provides a natural, esthetical look of the denture and provides that food parts are not captured in the interproximal gaps.

In some embodiments, the virtual outer gingival surface is generated in least in part by an offset of a corresponding portion of the digital 3D representation of the patient's gum.

This has the advantage that a natural appearance of this part of the denture easily can be obtained. Further the patient may experience less discomfort when wearing the denture if its outer surface resembles the natural anatomy of the patient's tissue. Also the designing of this part of the denture can be made highly automatic, e.g. by activating a virtual button on a user interface this part can be designed automatically.

In some embodiments, the virtual outer gingival surface is generated at least in part by a loofting process.

In some embodiments, at least part of the virtual outer gingival surface is shaped to resemble the corresponding surfaces in the patient's natural gum. The corresponding surfaces may relate to the visible part of the alveolar ridge and the palette, such that at least the visible surface of the gingival part of the denture is shaped according to the natural appearance of the patients gingival.

In some embodiments, at least part of the shape of the virtual outer gingival surface is selected from a gingival library.

This has e.g. the advantage that the denture can be designed quickly and to a large extent automatic. Using a gingival library with a selection of virtual outer gingival surface which appears natural provides that an esthetically appealing denture easily can be designed.

In some embodiments, at least part of the shape of the virtual outer gingival surface is modified or generated using a virtual free-form sculpt tool. This may be implemented by 3Shape Dental System's™ sculpt and edit tools which allow easily adding anatomical details to the gingiva with an operators own artistic touch In some embodiments, the virtual outer gingival surface is generated at least in part by a virtual marginal gingiva.

In some embodiments the virtual marginal gingiva is arranged at the gingival part of the denture where the gingiva meets the lingual, labial or buccal face of the virtual teeth models.

In some embodiments generating the virtual outer gingival surface comprises generating the virtual marginal gingiva and connecting the marginal gingiva to the gingival 3D spline.

In some embodiments generating the virtual outer gingival surface comprises connecting the gingival 3D spline to the virtual teeth models and then generating the marginal gingiva.

In some embodiments the gingival 3D spline is connected to a gingival-tooth line on the virtual teeth models.

In some embodiments the virtual outer gingival surface is configured to be adjusted.

An initial version of the virtual outer gingival surface may e.g. be selected from a library and the method may then comprise an adjustment of the selected initial version to personalize the virtual outer gingival surface to the patient's oral situation. This provides the advantage that an esthetically appealing denture which resembles the natural surface in the oral cavity easily can be designed.

In some embodiments the adjustment is performed by pulling in one or more control points arranged on the virtual outer gingival surface.

In some embodiments the virtual outer gingival surface is configured to be adjusted such that it curves inwards between the patient's gums and the gingival-tooth line on the teeth models.

An inward curvature between the gingival-tooth line and the gums provides a natural looking gingival part of the denture.

In some embodiments the method comprises virtually designing the outer gingival surface of the denture to be rounded off at the gingival edges or boundaries.

If the gingival edges or boundaries are rounded off it is most comfortable for the patient to wear the denture, since a gingival edge or boundary which is not rounded off will be quite uncomfortable for the patient since the edges and boundaries will then feel very sharp for the gums and when touched by the tongue.

In some embodiments the method comprises virtually designing the outer gingival surface of the mandible or lower jaw part of the denture to have a size big enough for the tongue to touch and rest on a part of the outer gingival surface. Hereby the tongue may act as an active prosthetic holder for the lower jaw part of the denture, which could otherwise have a tendency to fall back into the mouth.

In some embodiments the method comprises virtually designing a protrusion on the gingival edge or boundary of the palate or palette area of the denture. The function of the protrusion is to create a vacuum under the palate or palette area of the upper jaw denture, whereby the upper denture part will be sucked to the patient's own palate.

In some embodiments the method comprises virtually designing an indention in the center of the palate or palette area at the gingival edge or boundary of the denture.

Two salivary glands have their outlet at the palate and the denture should be designed not to cover these glands.

In some embodiments, the virtual outer gingival surface is generated at least in part by one or more virtual cervical protrusions. The virtual cervical protrusions may be configured to resemble the protrusions defined by the sub-gingival root ends of the teeth.

In some embodiments, the method comprises identifying an occlusal plane of the denture.

In some embodiments, the method comprises adjusting the bite height.

In some embodiments, the method comprises forming an upper wax rim for the patient's maxillary arch. In some embodiments, the method comprises scanning said upper wax rim to obtain a digital 3D representation of the upper wax rim.

In some embodiments, the method comprises forming a lower wax rim for the patient's mandibular arch. In some embodiments, the method comprises scanning said lower wax rim to obtain a digital 3D representation of the lower wax rim.

In some embodiments, the method comprises digitally forming a digital 3D representations of a lower wax rim for the patient's mandibular arch and/or digitally forming a digital 3D representations of an upper wax rim for the patient's maxillary arch, such as by selecting digital 3D representations of the wax rims from a wax rim library and digitally shaping these digital 3D representations to fit the patient's oral situation using a virtual manipulation tool.

Based on the digital 3D representations of the wax rims the location of the occlusal plane, the medial plane marked on a wax rim, or the incisal edge of anterior teeth of the mandibular can be obtained to e.g. derive the patient's occlusal plane. The wax rims can be obtained by scanning in the patient's mouth or by scanning a physical model, from a bite registration. The scanning may use desktop scanner or an intra-oral scanner.

The wax rims can be used for two functions, which is to adjust and ensure that the occlusion of the denture is correct, and to obtain the shape of the patient's lips, such that the teeth in the denture fits under the lips, without causing the lips to collapse into the mouth or causing the lips to be pushed away from their natural position.

In some embodiments the method comprises virtually arranging the teeth models relative to the digital 3D representations of the wax rim.

In some embodiments the arranged teeth models are virtually snapped to the digital 3D representation of the wax rim.

In some embodiments the teeth models are automatically arranged in a predefined distance from the digital 3D representation of the wax rim, such as at a predefined distance along a direction in the occlusal plane.

In some embodiments the centerline and/or the midline of the patient's face is recorded or sketched on the wax rims.

The recorded centerline and midline is used when designing the denture, such that the artificial teeth in the denture is arranged aesthetically and/or functionally correct relative to the patient's face.

In some embodiments, the method comprises obtaining digital 3D representations of both the patient's mandibular gum and maxillary gum.

In some embodiments, the method comprises arranging physical models of the patient's mandibular and maxillary and the corresponding lower and upper wax rims in a stack according to their relative position in occlusion, and obtaining a digital 3D representation of this stack.

The stack may be scanned before the gum models, or after the gum models. In one work flow the stack is arranged and scanned. Then the physical model of the maxillary and the wax rims are removed and scanned together. Finally the physical model of the mandibular is scanned.

In some embodiments, the method comprises virtually aligning the digital 3D representations of the patient's mandibular and maxillary gums and the digital 3D representation of the stack, such that a combined gum-wax rim model is generated.

In some embodiments, gum-wax rim models are defined for each of the maxillary and the mandibular.

This provides e.g. the advantage that the gum-wax rim models can be arranged together to provide information of the relative arrangement of the gums in occlusion.

In some embodiments, the relative arrangement of the gum of the maxillary arch and the occlusal plane is derived. In some embodiments, the relative arrangement of the gum of the mandibular arch and the occlusal plane is derived. In both cases it can be derived from the digital 3D representation of the stack.

In some embodiments, the method comprises obtaining a digital 3D representation of the lower wax rim, such as by scanning the formed upper wax rim.

This has the advantage that the digital 3D representation of the lower wax rim can be used in the digital designing of the denture, such that the information of provided by the lower wax rim can be utilized.

In some embodiments, the method comprises obtaining a digital 3D representation of the upper wax rim, such as by scanning the formed upper wax rim.

This has the advantage that the digital 3D representation of the upper wax rim can be used in the digital designing of the denture, such that the information of provided by the upper wax rim can be utilized.

In some embodiments, the digital 3D representations of the upper and lower wax rims are virtually brought into occlusion, and where the position and orientation of the occlusal plane is determined therefrom. The relative arrangement of the mandibular and maxillary arch in occlusion can also be determined therefrom.

In some embodiments, the digital 3D representations of the upper and lower wax rims are virtually arranged in relation to the digital 3D representation of the patient's mandibular and maxillary gums such that the combined gum-wax rim model is generated.

In some embodiments, the lip line of the denture is derived from the combined gum-wax rim model.

In some embodiments, the incisal edge of the anterior teeth of the mandibular denture is derived from the combined gum-wax rim model.

In some embodiments, the occlusal plane is derived from the combined gum-wax rim model.

In some embodiments, the incisal edge of the anterior teeth of the maxillary denture is derived from the combined gum-wax rim model.

The incisal edge of maxillary anterior teeth may be marked on the upper wax-rim in cases where the maxillary anterior teeth extend below the incisal edge of the mandibular anterior teeth.

In some embodiments the occlusion or occlusal plane of the patient's mouth is derived from the upper and lower wax rims.

The derived occlusion or occlusal plane of the mouth can be provided as the occlusal plane or occlusion of the denture.

In some embodiments the shape of the patient's lips is derived from the upper and lower wax rims.

The derived shape of the lips can be used when designing the denture. Thus it can be determined from the wax rims how much space there is available for the denture teeth and gingiva behind the lips. The denture teeth and the gingival part should not take up more or less space than appropriate, since otherwise the patient's lips will not cover the denture in an esthetic way.

In some embodiments the teeth models is virtually snapped to the inside of the digital 3D representation(s) of the wax rim(s) for ensuring that there is sufficient space for the teeth behind the patient's lips.

Alternatively the teeth models may be snapped to the digital 3D representation of the wax rim in a suitable place for ensuring that there is sufficient space for the teeth behind the patient's lips.

In some embodiments, the virtual teeth models are virtually arranged in relation to the digital 3D representation of the patient's gum based on a visualization of the virtual teeth models relative to said combined gum-wax rim model.

In some embodiments, virtually arranging the virtual teeth models in relation to the digital 3D representation of the patient's gum comprises rotating and/or translating the virtual teeth models with respect to the digital 3D representation of the patient's gum.

In some embodiments, the method comprises virtually arranging at least the teeth part of the denture in relation to a virtual articulator and performing a dynamic virtual articulation to evaluate the occlusion of the denture.

In some embodiments, the method comprises determining a target form of the denture teeth. The target form may be determined using collision detection based on e.g. a virtual dynamical articulator, a target relationship between the teeth and the gums, the available space for the denture gingival material.

Virtual articulation can be performed using a virtual articulator comprising a virtual 3D model of the maxillary and a virtual 3D model of the mandibular with the corresponding teeth arranged relative to their respective jaws. The virtual maxillary and the virtual mandibular are moved relative to each other for simulating dynamic occlusion such that collisions between teeth in the virtual maxillary and virtual mandibular occur.

The articulation and occlusion of the denture can be evaluated using a virtual dynamical articulator in which the denture and the antagonist teeth are arranged. The antagonist teeth can be the virtual teeth models of a denture modeled simultaneously or previously for the opposing arch. The antagonist may also be original teeth of the patient. For the case where the patient's mandibular teeth are intact and a maxillary denture is to be modeled, the antagonist teeth will be the intact set of teeth of the mandibular.

In some embodiments the method comprises:
performing virtual articulation of the denture, and
virtually removing a part of one or more of the teeth models, if the virtual articulation indicates that removal is suitable.

The virtual removal of part of the virtual teeth models may be performed automatically based on the articulation or may be removed virtually by the operator.

In some embodiments the method comprises:
performing virtual articulation of the denture, and
virtually adjusting the position and/or orientation of one or more of the teeth models, if the virtual articulation indicates that adjustment is suitable.

The virtual adjustment of position and/or orientation of part of the virtual teeth models may be performed automatically based on the articulation or may be performed virtually by the operator. The teeth models may for example be translated in the labial or lingual direction or be moved further into the gingiva part or be rotated relative to the neighbor teeth.

In some embodiments, the virtual teeth models correspond to exact versions the denture teeth, such as exact versions of pre-manufactured denture teeth. An initial virtual model of a tooth may correspond to the exact version of a denture tooth.

In some embodiments, the denture teeth are pre-manufactured teeth, such as pre-manufactured acrylic teeth. Such pre-manufactured teeth may for example be Vita T3M or other denture teeth manufactured by VITA Zahnfabrik in Germany, or Ivoclar Vivadent artificial teeth, such as Phonares, Vivodent, VivoTAC, Ivostar etc.

In some embodiments, the method comprises adjusting the size, shape, length, width, or thickness of the pre-manufactured teeth to obtain said target form. The adjustments may involve the removal of excess tooth material by e.g. grinding or laser ablation. The adjustments may also involve addition of tooth material such as by locally adding porcelain material to selected parts of the tooth.

In some embodiments, the denture teeth are customized teeth which are represented by CAD teeth models.

The CAD teeth models of the denture teeth may be modified with respect to their size, shape, length, width, distribution of mass, or thickness to obtain said target form. This can be done during the modeling of the digital design of the denture, such that the tooth shape also is taken into consideration in designing the gingival part of the denture.

In some embodiments, the digital 3D representation of the patient's gum is obtained by scanning the patient's gingival using an intraoral scanner.

In some embodiments, the digital 3D representation of the patient's gum is obtained by scanning at least part of an impression of the patient's gum and/or by scanning at least part of a physical model of the patient's gum. The scanning can be performed by means of laser light scanning, white light scanning, probe-scanning, X-ray scanning, and/or CT scanning.

In some embodiments, the method is for modeling a maxillary or a mandibular denture. For example, the teeth of the maxillary may be intact while a denture is designed for its antagonist, i.e. the mandibular, or vice versa.

In this case, the teeth of the antagonist are scanned and a digital 3D representation of the antagonist is obtained. When arranging the virtual teeth models of the denture, the digital 3D representation of the antagonist is then used when e.g. applying a virtual dynamical articulator to evaluate the occlusion.

In some embodiments, the method is for modeling a maxillary and a mandibular denture.

Virtual teeth models are then obtained for both the maxillary and the mandibular denture, and the virtual models of the mandibular teeth are preferably taken into account when arranging the virtual model of the maxillary teeth and vice versa.

In some embodiments, at least the teeth part of a maxillary and the teeth part of a mandibular denture are modeled simultaneously. The virtual models of the mandibular teeth and the virtual models of the maxillary teeth may be positioned, rotated, resized etc. depending on each other's position, rotation, size, etc.

In some embodiments, the method is for modeling a full denture, i.e. a denture which replaces all teeth in the corresponding part of the patient's mouth.

Some of the patient's original teeth may be present in the digital 3D representation of the patient's gums, and in some cases these teeth are so healthy that they preferably should be preserved. In some embodiments, the method is for modeling a partial denture, i.e. a denture which replaces some teeth in the corresponding part of the patient's mouth.

In some embodiments, at least part of the method is computer-implemented. This has the advantage that many design steps can be performed faster and with higher precision than when an operator is doing them manually.

In some embodiments, the extent of undercut sections between the denture and the gums is controlled. For a maxillary denture the suction power between the denture and the patient's gums counteracts the gravitational force to keep the denture fixated at the patient's maxillary gums. For this denture a certain degree of undercuts may assist the suction power and actually work to the benefit of the patient.

For the mandibular denture it may be advantageous to block-out any undercuts.

In some embodiments the method comprises performing a partial wax block-out of undercuts.

Especially for elder people, as wax block-out may be required for ensuring that the denture stays in the patient's mouth.

In some embodiments, the method comprises mirroring of teeth.

The mirroring of teeth may be such that the arrangement of denture teeth on one side of an arch is determined by mirroring the arrangement of the denture teeth on the opposite side of the arch, such as mirroring with respect to the patient's medial plane.

In some embodiments the mirroring of teeth is such that the shape of the denture teeth on one side of an arch is determined by mirroring the shape of the denture teeth on the opposite side of the arch. The mirroring may thus be with respect to the patient's medial plane.

It is an advantage that mirroring can be performed, because then the user does not need to work on or modify the arrangement or shape of all teeth which should be designed with respect to arrangement and shape, the user can just design teeth in e.g. the left arch. One or more teeth can be mirrored.

In some embodiments, the result of the modeling of the digital denture designs is a virtual model of the denture which is completely ready for efficient output on a variety of milling machines or 3D printers.

The method may comprise producing the denture's gingiva to match perfectly pre-manufactured acrylic teeth or custom manufactured teeth. Often, the denture teeth are made from a first material and the gingival part is manufactured in a second material.

In some embodiments the method comprises virtually arranging one or more implants relative to the virtual teeth models and the gingival part of the denture.

In some embodiments the method comprises virtually connecting one or more of the virtual teeth models and/or the gingival part of the denture to the one or more implants.

The implants are connected on the underside of the gingival part, i.e. on the part of the gingival part facing towards the patient's gums, since the implants are implanted in the patient's gums.

Thus no superstructure, bar, frame etc. in the denture may be required for connecting the denture to implants.

In some embodiments the method comprises virtually cutting back or offsetting the virtual teeth models.

In some embodiments a veneering layer may be virtually designed on virtually cut backed or offsetted teeth.

In some embodiments the virtual model teeth are configured for being virtually reduced in size.

When the virtual teeth models correspond to physical pre-manufactured teeth, these pre-manufactured teeth can only be made smaller not bigger, and therefore the software used for designing the virtual teeth models may ensure that the operator or dental designer can only reduce the size of the virtual model teeth, not increasing the size of a virtual model tooth. If the dental technician wishes to have a bigger tooth, he/she should select a different model tooth from the digital library of teeth.

In some embodiments the method comprises virtually arranging a 2D image of the patient's lips relative to the digital design of the denture.

It is an advantage that the design of the denture can be viewed or visualized relative to the patient's own lips for showing the expected final result to the patient for approval. The 2D image and the digital design of the denture may be aligned.

Further details relating to arranging a 2D image of the patient's lips relative to the digital design of the denture can be found in 3Shape's patent application WO2012/000511.

In some embodiments the method comprises virtually arranging and aligning a 2D image of the patient's lips relative to the digital 3D representations of the wax rims.

The wax rim may be marked with markers for certain points or areas, for example with holes in the wax indicating the smile line, the canines etc.

In some embodiments the method comprises defining the thickness of the gingival part of the denture.

The thickness may be different in different areas of the gingival part. For example may the thickness of the gingival be smaller at the boundaries or edges of the gingival, such that the transition between the gingival part and the patient's gum will look as natural as possible by means of a smooth transition.

The present invention relates to different aspects including the method and system described above and in the following, and corresponding methods, and systems, each yielding one or more of the benefits and advantages described in connection with the first mentioned aspect, and each having one or more embodiments corresponding to the embodiments described in connection with the first mentioned aspect and/or disclosed in the appended claims.

In particular, disclosed is a method for manufacturing a denture for a patient, where the denture comprises a gingival part and denture teeth, wherein the method comprises:
 obtaining a digital denture design, where the digital denture design is modeled using the method according to any of the embodiments;
 manufacturing at least part of the denture by means of computer aided manufacturing (CAM).

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

Disclosed is also a nontransitory computer readable medium storing thereon a computer program, where said computer program is configured for causing computer-assisted modeling a digital design of a denture for a patient, said denture comprising a gingival part and a teeth part comprising a set of denture teeth, where the modeling comprises: obtaining a digital 3D representation of the patient's gum, obtaining virtual teeth models corresponding to the denture teeth, virtually arranging the virtual teeth models in relation to the digital 3D representation of the patient's gum, and generating a virtual outer gingival surface of the gingival part of the denture.

Disclosed is also a system for modeling a digital design of a denture for a patient, said denture comprising a gingival part and a teeth part comprising a set of denture teeth, where the system comprises
 a scanner unit configured for obtaining a digital 3D representation of the patient's gum,
 a unit configured for obtaining virtual teeth models corresponding to the denture teeth;
 a nontransitory computer readable medium having one or more computer instructions stored thereon, where said computer instructions comprises instructions for virtually arranging the virtual teeth models in relation to the digital 3D representation of the patient's gum, and generating a virtual outer gingival surface of the gingival part of the denture.

Disclosed is a user interface for modeling a digital design of a denture for a patient, said denture comprising a gingival part and a teeth part comprising a set of denture teeth, where the user interface is configured for:
 visualizing a digital 3D representation of the patient's gum and virtual teeth models corresponding to the denture teeth;
 virtually arranging the virtual teeth models in relation to the digital 3D representation of the patient's gum; and
 generating a virtual outer gingival surface of the gingival part of the denture.

In some embodiments, the user interface is configured for being visualized to an operator using a computer screen and for allowing the operator to enter data into and make choices presented in the user interface by means of a computer keyboard or a computer mouse.

In some embodiments, the user interface is configured for obtaining and visualizing digital 3D representations of an upper and/or a lower wax rim together with the digital 3D representation of the patient's gum and/or the virtual teeth models corresponding to the denture teeth.

The user interface can be implemented using a computer system where the user interface is visualized using a computer screen showing the different components of the user interface, such a data entry fields and virtual push buttons configured for performing one or more steps of a method according to an embodiment of the invention. Data entry means such as a computer mouse and a computer keyboard can be connected to the computer system and used for entering data into the user interface and for making selections by e.g. pressing said virtual push buttons using the computer mouse.

In some embodiments, the user interface is configured for allowing an operator to carry out a method according to an embodiment of the invention. Preferably, at least one of the steps of obtaining a digital 3D representation of the patient's gum, obtaining virtual teeth models corresponding to the denture teeth, and generating a virtual outer gingival surface of the gingival part of the denture can be performed by the operator using said user interface. In some embodiments, the steps of the method are performed sequentially and the user interface can be configured for sequentially providing a visually representation of the steps to the operator such that the sequence of the user interface matches that of the method. In some embodiments, the user interface is configured for simultaneously providing a visually representation of two or more of the steps to the operator.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

Figure 1A:
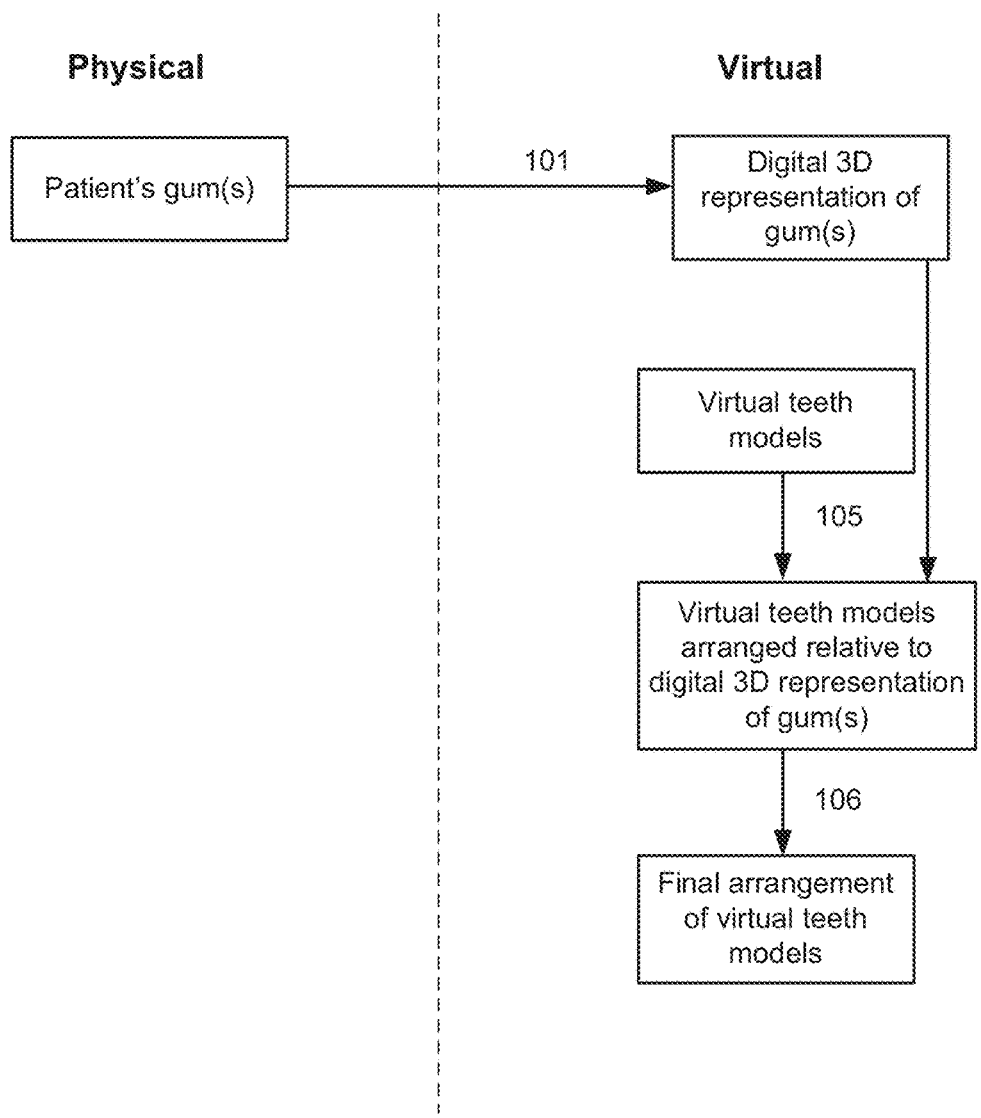
FIG. 1 shows a flowchart of an embodiment of the invention.

In the following description, reference is made to the accompanying figures, which show by way of illustration how the invention may be practiced.

The digital 3D representation of the patient's gums can be obtained by directly scanning the patient's gums using an intra-oral scanner or by scanning an impression or a physical model of the gums. The intra-oral scanner may be configured for utilizing focus scanning, where the digital 3D representation of the scanned teeth is reconstructed from in-focus images acquired at different focus depths, such as the TRIOS intra-oral scanner from 3Shape TRIOS A/S. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions. The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

An impression or a physical model of the patient's gums can also be scanned using for example a desktop scanner based on e.g. the triangulation scheme. A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time. An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

A digital 3D representation of an object can be a mathematical representation of the 3D surface of the object derived from scan data using specialized software. The product is often called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D modeling is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

Some 3D scanners collect distance information about surfaces within its field of view. The "picture" produced by a 3D scanner describes the distance to a surface at each point in the picture. For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

Figure 1B:
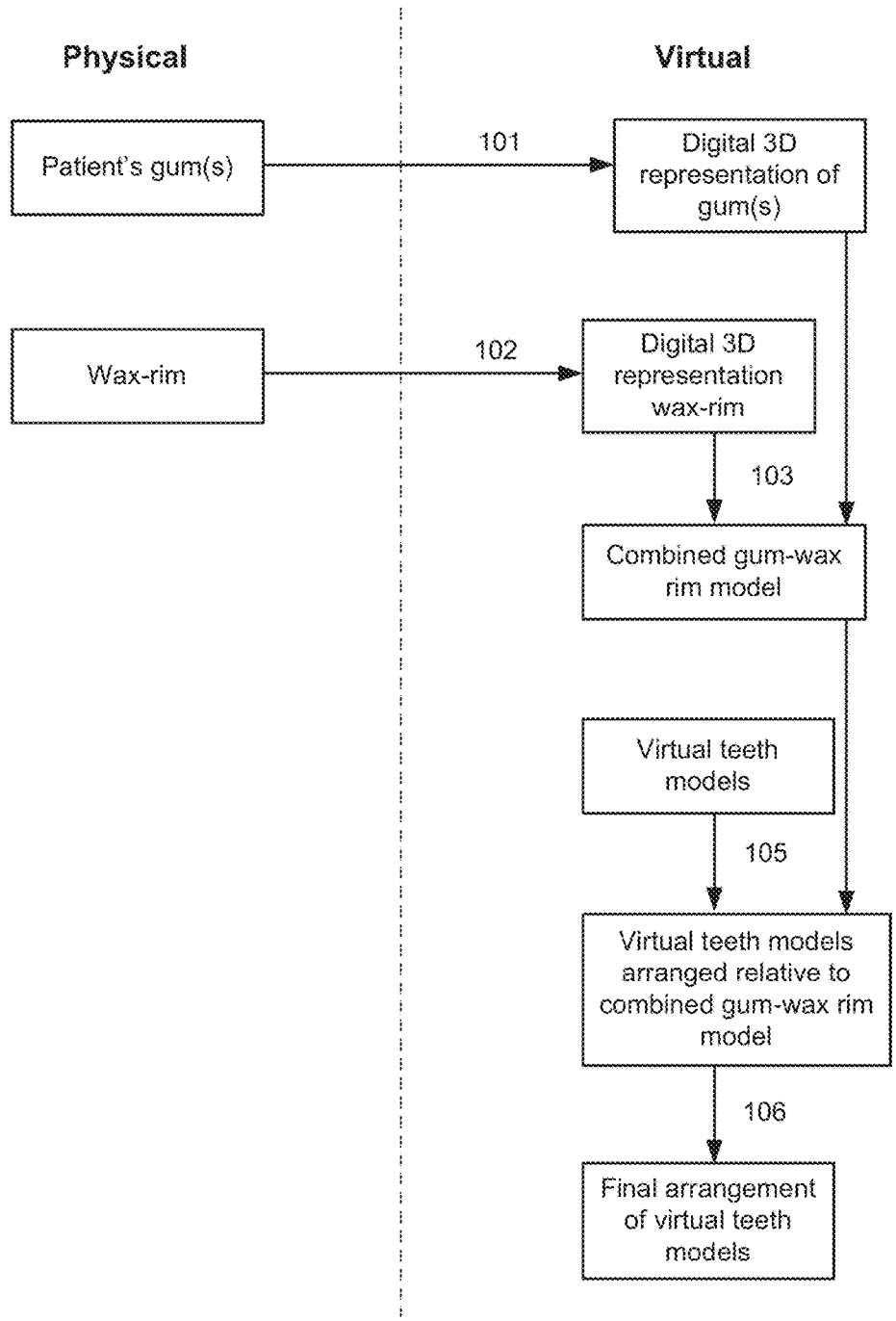
Figure 1C:
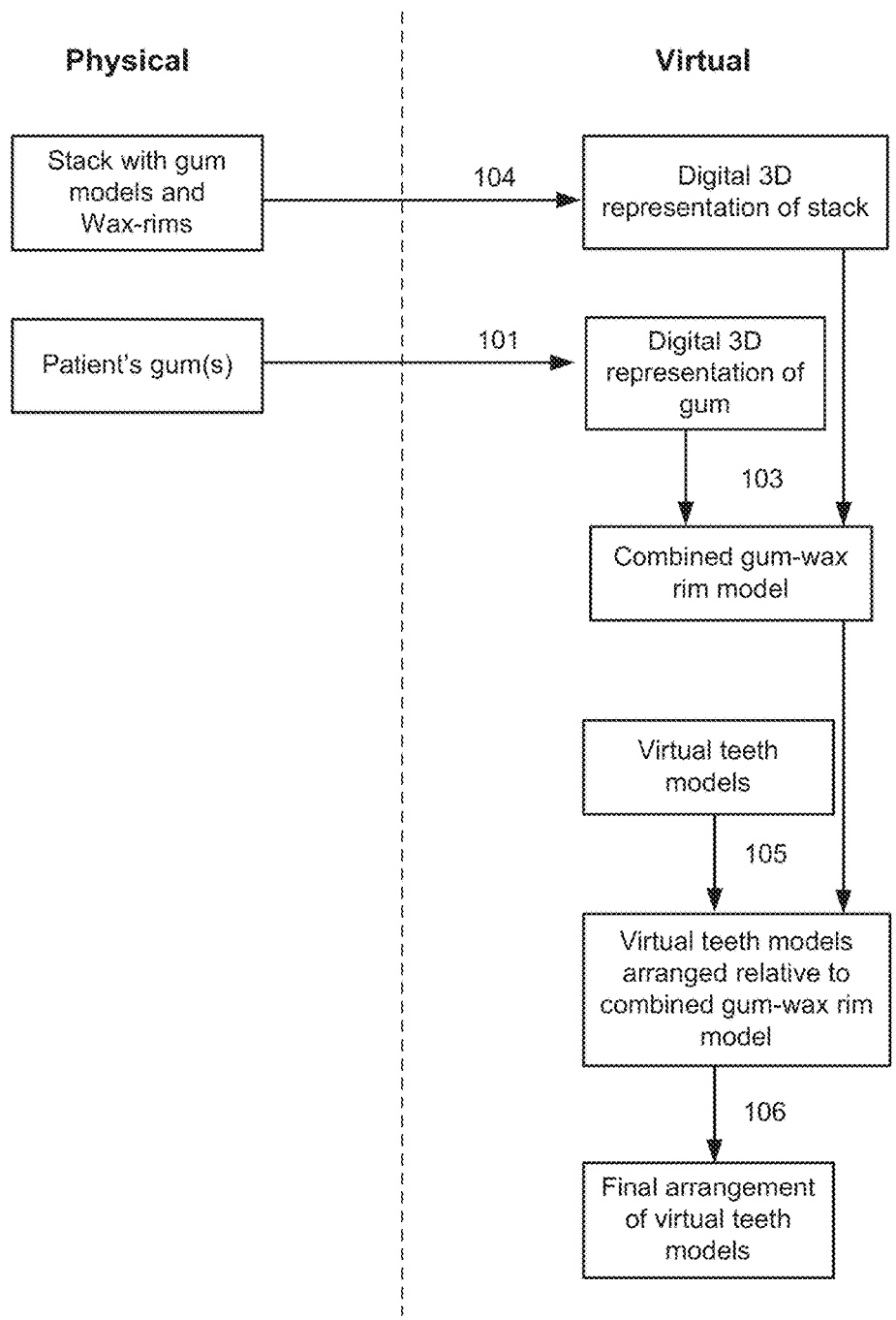
Figure 1D:
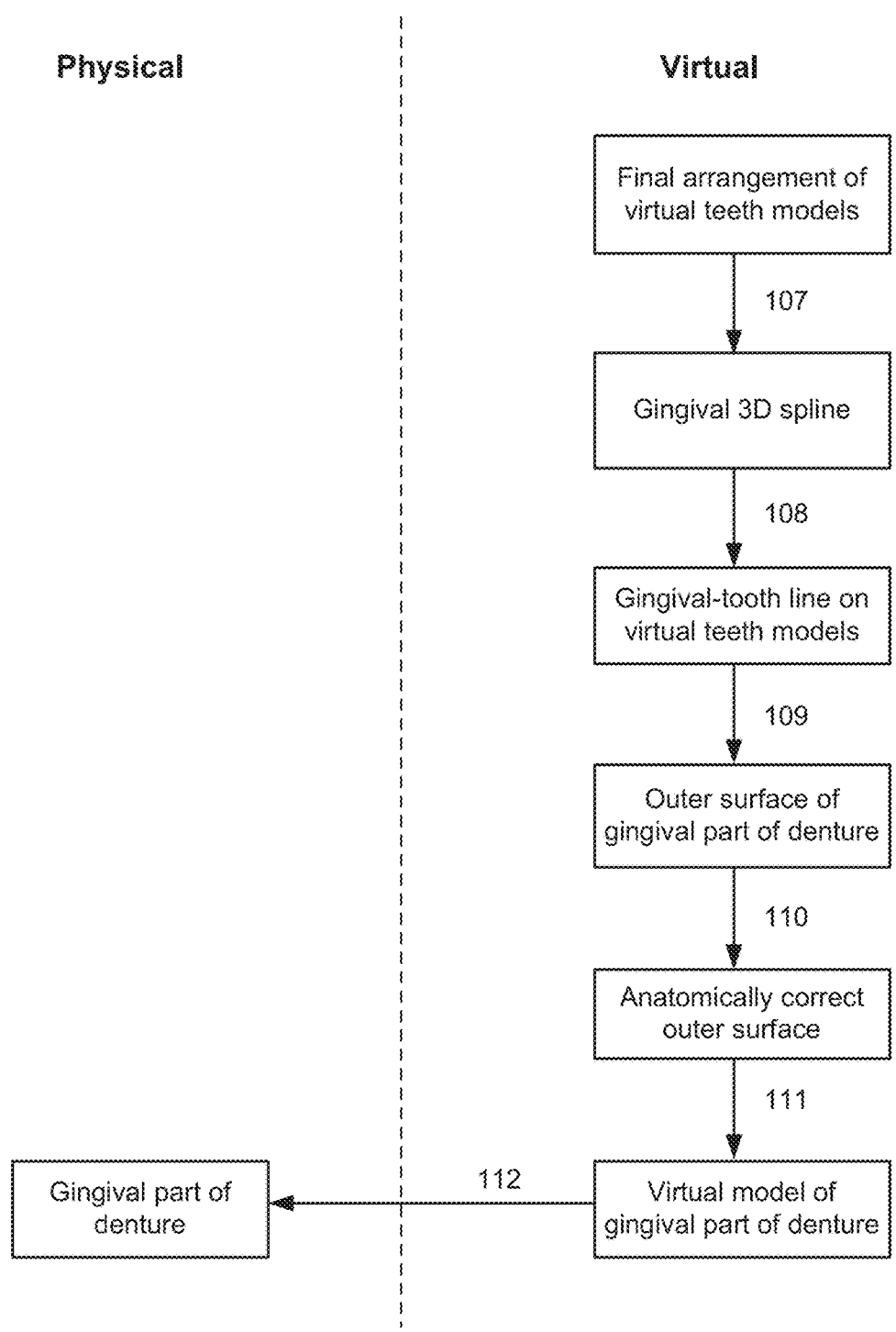

FIG. 1 show flowcharts of embodiments of the invention, with FIG. 1a-1c illustrating some initial steps and FIG. 1d showing some subsequent steps. The vertical dotted line at the center of the page divides the flowchart into a part relating to physical units and a part relating to virtual units.

In step 101 a digital 3D representation of the patient's gums is obtained by e.g. scanning the patient's gums using an intra-oral scanner and converting the data obtained by the scanner to a 3D model of the gums. The digital 3D representation of the patient's gums comprises at least the alveolar ridge at which the denture is intended to be placed. In case the patient has any teeth that are to be preserved, these should preferably also be part of the digital 3D representation.

In step 105, virtual teeth models and the digital 3D representation of the patient's gums are combined, e.g. by overlaying the virtual teeth models on the digital 3D representation of the patient's gums, such that the virtual teeth models are arranged relative to the digital 3D representation of the patient's gums. The denture teeth can be prefabricated teeth such as the Vita T3M teeth and the corresponding virtual teeth models are stored in a memory unit of a computer system in which the method is implemented.

The arrangement of the virtual teeth models relative to the digital 3D representation of the patient's gums and the arrangement of the virtual teeth models relative to each other can be modified to obtain an aesthetic appearance and a correct occlusion of the teeth in the later manufactured denture. The modification can be performed manually or automatically using computer implemented algorithms based on e.g. a virtual dynamical articulation and/or a visualization of the virtual teeth models together with an image of the patient's face.

The method can utilize collision mapping relative to the antagonist when evaluating the design of a denture. It can be an advantage that the collision mapping with the antagonist can be provided, because hereby it is easy and fast for the user to check if there is actually space enough for the designed denture and its teeth in the mouth of the patient. The collision detection can examine the spatial arrangement of the virtual teeth models, such as the position, direction, rotation, height etc. of the teeth relative to each other.

In FIG. 1b is illustrated an additional step compared to FIG. 1a. Wax-rims are formed for the upper jaw (maxillary) and lower jaw (mandibular) and in step 102 a digital 3D representation of the wax rim is obtained. The digital 3D representation of the wax rim is combined with the digital 3D representation of the patient's gums in step 103 to provide the combined gum-wax rim model.

The virtual teeth models are then arranged relative to the combined gum-wax rim model and the final arrangement of the virtual teeth models can be determined.

The combination of the digital 3D representation of the wax rim, the digital 3D representation of the patient's gums, and the virtual teeth models can also be such that the virtual teeth models are arranged relative to the digital 3D representation of the wax rim and the digital 3D representation of the patient's gums is added subsequently, or such that the virtual teeth models are arranged relative to the digital 3D representation of the gums and the digital 3D representation of the patient's wax rim is added subsequently.

In FIG. 1c, a stack with physical models of the patient's mandibular and maxillary and the corresponding lower and upper wax rims arranged according to their relative position in occlusion is scanned 104 such that a digital 3D representation of this stack is obtained.

In step 101 digital 3D representations of both the patient's gums are obtained by e.g. scanning the patient's gums using an intra-oral scanner. The digital 3D representations of the patient's gums comprise at least the alveolar ridge at which the dentures are intended to be placed.

The digital 3D representations of the patient's mandibular and maxillary gums and the digital 3D representation of the stack are then aligned 103, such that a combined gum-wax rim model is generated.

In the combined model the portion corresponding to the patient's mandibular and maxillary gums in the digital 3D representation of the stack may be subtracted such that in a visualization of the combined model, the digital 3D representations of the patient's mandibular and maxillary gums can be seen together with the wax rim portions of the digital 3D representation of the stack.

The stack may be scanned before or after the gum models.

In step 105, the virtual teeth models are arranged relative to the combined gum-wax rim model, e.g. by overlaying the virtual teeth models on the combined gum-wax rim model and their arrangement is optimized 106 to provide a final arrangement of the virtual teeth model relative to the combined model.

FIG. 1d shows some subsequent steps, i.e. after the final arrangement of the virtual teeth models is determined.

In step 107, a gingival 3D spline is defined using e.g. a pointer tool, such as a mouse, to identify the shape of the gingival 3D spline and its position relative to the digital 3D representation of the gums.

In step 108, a gingival-tooth line is defined on the virtual teeth models. This line marks where on the denture teeth the gingival part of the manufactured denture will contact the denture teeth of the denture.

In step 109, the outer surface of the gingival part of the denture is virtually generated. This can be done by offsetting a corresponding surface of the digital 3D representation of the patient's gums and/or by a loofting process connecting e.g. an offset gum surface and a gingival-tooth line at the virtual teeth models. The outer surface can be generated such that the natural appearance of a gingival is mimicked by the gingival part of the denture. This can be achieved by adding a virtual marginal gingiva and/or virtual rugae to the virtual outer gingival surface such that an anatomical correct outer surface is obtained (step 110).

In step 111, a full virtual model of the gingival part of the denture is provided by e.g. forming a gingival facing surface of the gingival part of the denture. This can be formed as an offset of the digital 3D representation of the patient's gum(s).

The gingival part of the denture can then be manufactured in step 112 using CAM equipment operated to manufacture the generated virtual model of the gingival part of the denture.

FIGS. 2 to 5 show some steps in modeling the digital design of a denture. The figures show cross sectional representations of the virtual teeth models and the digital 3D representation of the patient's gums at one position along the alveolar ridge of the patient's gums.

Figure 2A:
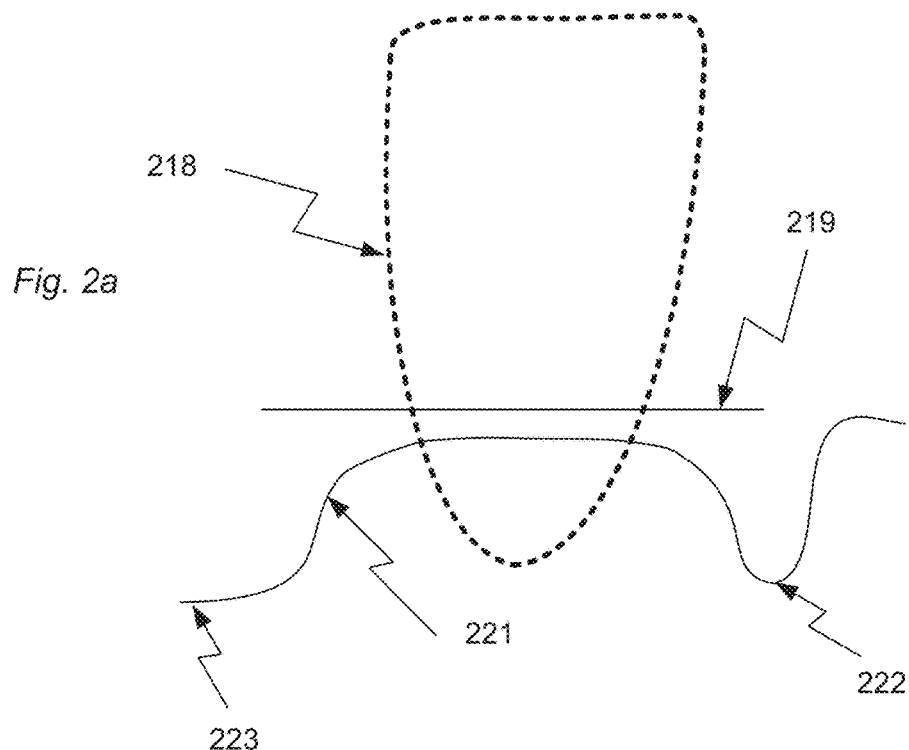
FIGS. 2 to 5 show some steps in modeling the digital design of a denture.

In FIG. 2a, an initial virtual model of a tooth 218 is arranged relative to the alveolar ridge 221 of a digital 3D representation of the patient's gum according to a final arrangement, i.e. where the occlusion and aesthetics of the denture teeth has been modified/evaluated. An off-set line 219 configured for marking the lower limit of the denture teeth relative to the gingival part of the denture is indicated. This off-set line defines a section of the virtual tooth model which is to be cut away in order to prevent collisions with the patient's gums and to make space for gingival material between the gums and the denture teeth.

Figure 2B:
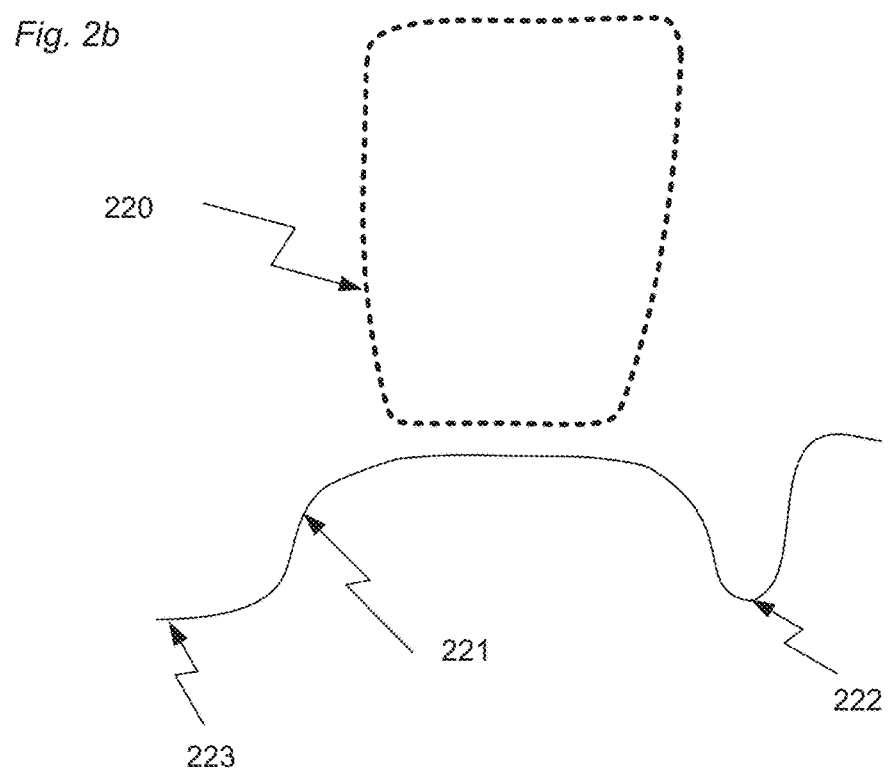

When the initial virtual tooth model 218 is cut to the off-set line 219 it is shaped according to the virtual tooth model 220 seen in FIG. 2b. In several of the following figures, the step of cutting the virtual tooth model to off-set line could also be performed after the design of the gingival part of the denture was done.

In the figure, the sulcus part 222 and the palette part 223 of the patient's gum are also indicated.

Figure 3:
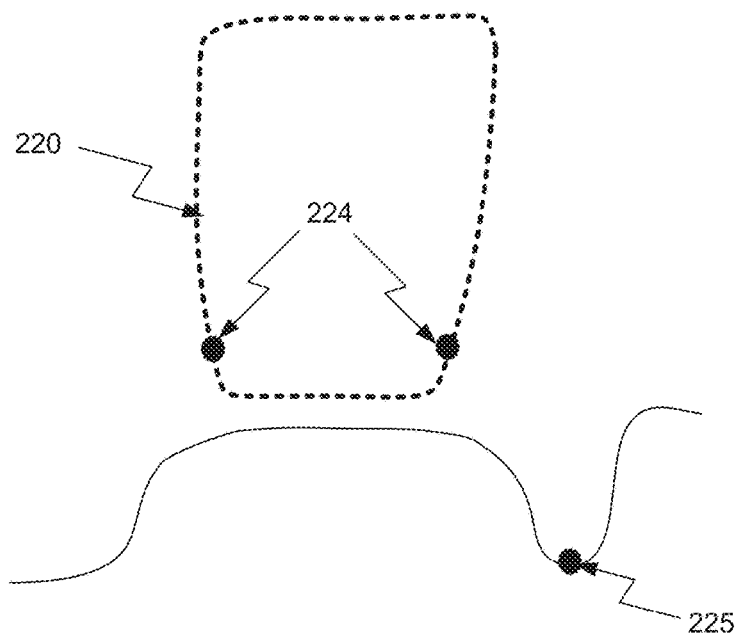

In FIG. 3, a gingival-tooth line 224 is indicated on the virtual teeth model and agingival 3D spline 225 is defined at the sulcus part. The gingival 3D spline 225 can be defined automatically using computer implemented algorithms configured for identifying the sulcus or by user provided inputs using e.g. a computer mouse.

Figure 4:
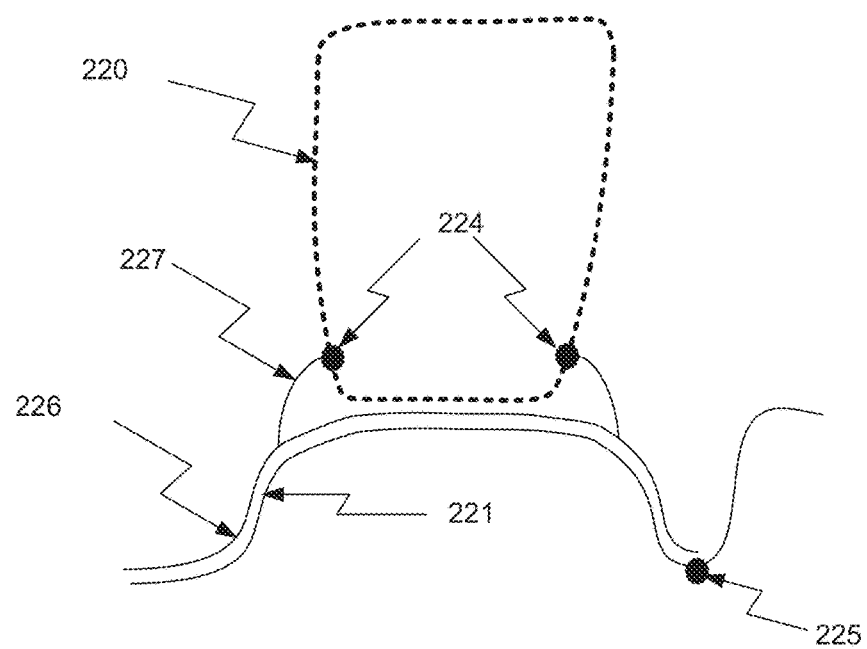

In FIG. 4, an offset surface 226 is defined by offsetting the digital 3D representation of the patient's gums over the palette and the alveolar to the gingival 3D spline 225, such that the gingival 3D spline defines the boundary of the denture. A virtual marginal gingiva 227 is added to improve the aesthetic appearance of the denture. The virtual outer gingival surface can be formed by interpolation, such as by spline based transition and interpolation of the surface.

Here the offset of the surface is uniform but it may also be non-uniform with a larger offset at the alveolar ridge compared to the offset at the gingival 3D spline such that the gingival part is thicker at the teeth part than at the boundary.

The offset at the alveolar ridge may be such that the denture reaches the position where the denture teeth are to be placed. The virtual model of the gingival part of the denture may then be formed by a Boolean subtraction process.

Figure 5:
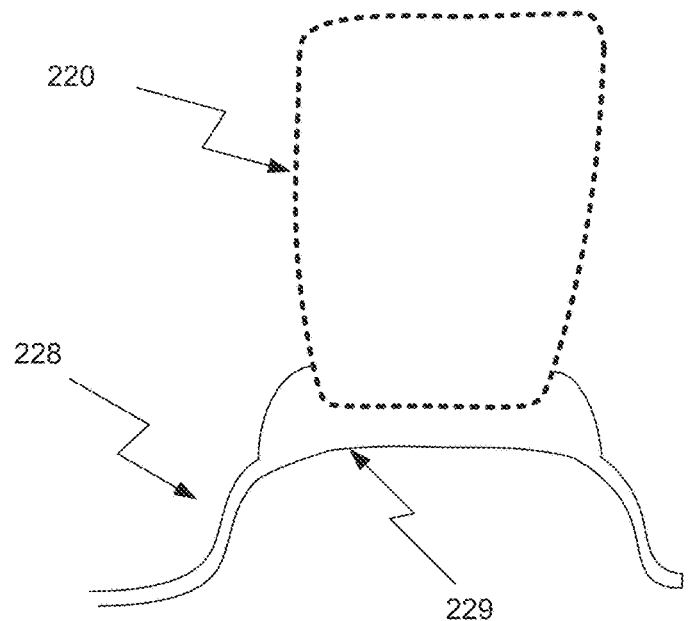

In FIG. 5, the virtual outer gingival surface 228 of the gingival part of the denture is formed as well as the gingival facing surface 229, such that the gingival part of the denture can be manufactured using CAM techniques based on this virtual model. The gingival facing surface of the denture may be defined as an offset of the digital 3D representation of the patient's gum such that it automatically is configured to follow the shape of the patient's gums.

Figure 6:
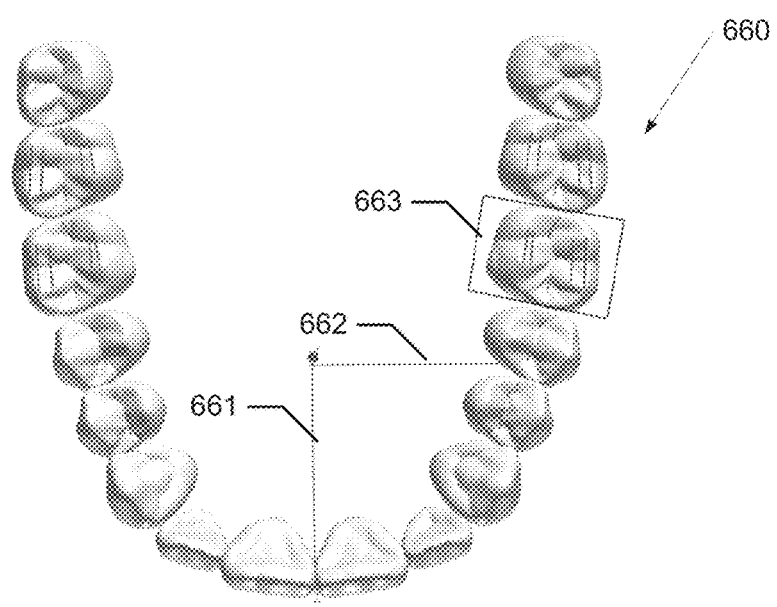
FIG. 6 shows how mirroring can be applied in the modeling of the denture.

FIG. 6 shows an example of mirroring in relation to a set of virtual teeth models corresponding to the denture teeth of a maxillary denture.

The set of teeth 660 can be selected from an electronic library containing a number of different set of teeth, or the operator can design the set of teeth himself by defining one or more parameters for the teeth. The virtual teeth models in the set of teeth can be selected based on a number of parameters, such as size, shape etc.

The patient's median line 661 is shown and a line 662 perpendicular to the median line is shown. The function of the line 662 is for improved visual direction for the user. Thus a global coordinate system for the complete composed set of teeth is defined, whereby rotation, positioning etc. can be controlled for the complete composed set of teeth. When modeling a full denture, e.g. a full maxillary denture, the arrangement of the virtual teeth model in e.g. the left side may be determined and the arrangement of the virtual teeth models then mirrored to the right side of the denture.

The individual teeth in the set of teeth 660 may also be modified individually. A tooth may for example be rotated relative to the patient's median line. The box 663 around the first molar tooth indicates that a coordinate system can be defined for each tooth, whereby rotation, positioning etc. can be controlled for each individual tooth. In a computer implementation of the invention, a coordinate system specific for the tooth can be shown on the tooth indicating to the user that that the program is in the mode, where the individual tooth can be modified with respect to positioning, e.g. rotation, translation etc. The denture teeth can also be modified for example with respect to shape, e.g. length, thickness, distribution of mass etc. The denture teeth may be pre-determined teeth where the size may be reduced by e.g. grinding.

FIGS. 7-13 show screen shots from a computer-implemented embodiment of the invention.

Figure 7:
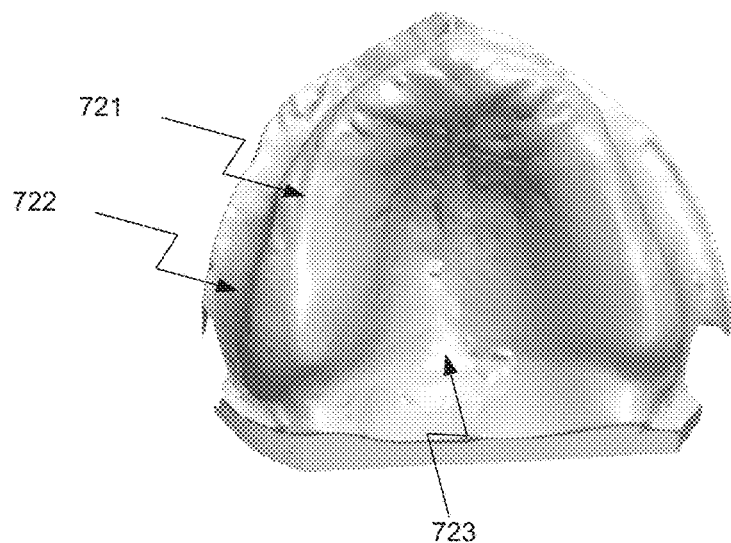
FIG. 7 shows an obtained digital 3D representation of the gingiva for an edentulous upper jaw (maxilla).

FIG. 7 shows an obtained digital 3D representation of the gingiva for an edentulous upper jaw (maxilla). The digital 3D representation can be obtained by directly scanning the patient's gingival using an intra-oral scanner such as the TRIOS intra-oral scanner from 3Shape. In the digital 3D representation the alveolar ridge 721, the sulcus 722 and the palette 723 of the patient's gum are seen.

Figure 8:
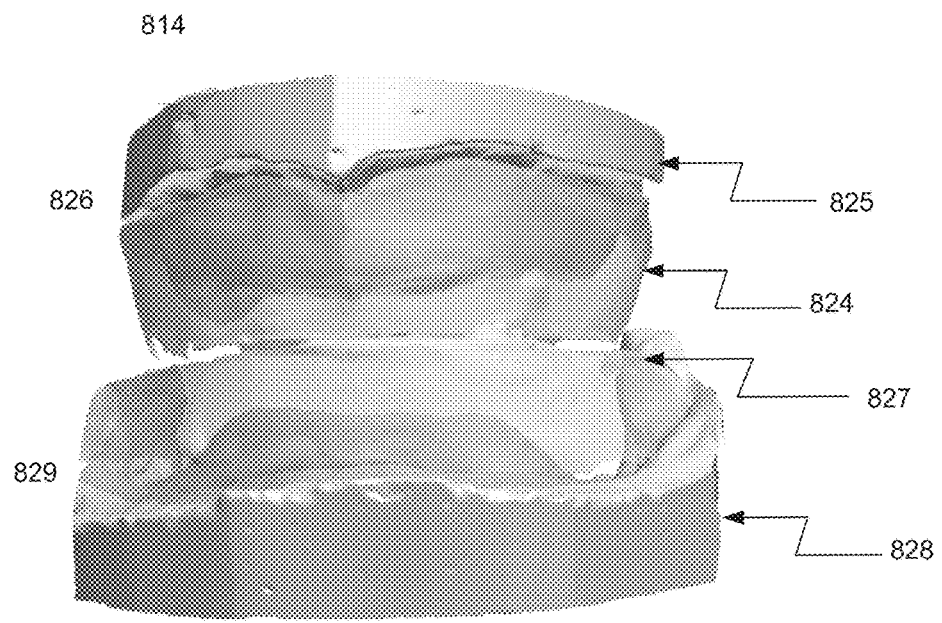
FIGS. 8 and 9 illustrate the use of digital 3D representations of the wax rims when arranging the virtual teeth models.
Figure 9:
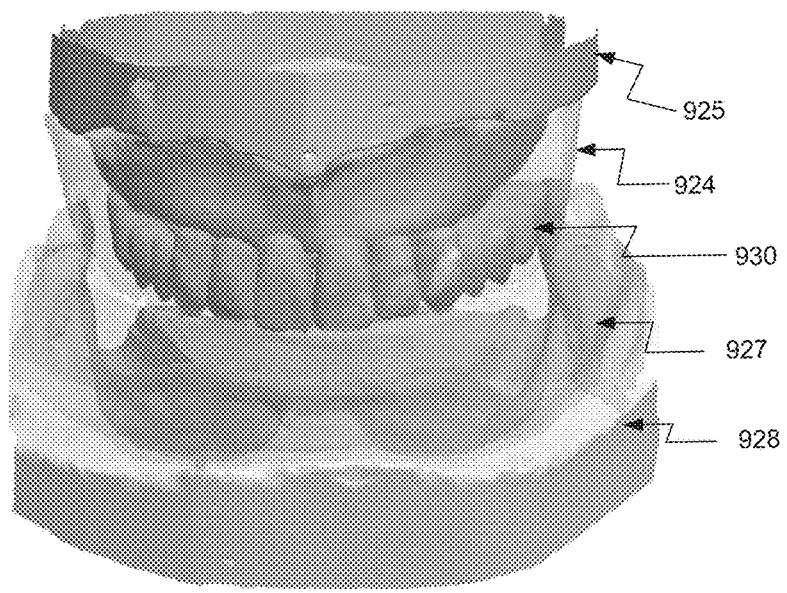

FIGS. 8 and 9 illustrate the use of digital 3D representations of the wax rims when arranging the virtual teeth models.

The arrangement of the virtual teeth models may involve forming an upper wax rim for the patient's upper jaw (the maxillary arch) and a lower wax rim for the patient's lower jaw (the mandibular arch). The wax rims are formed such that their interface when arranged in the patient's mouth is aligned with the patient's occlusal plane.

In some embodiments, three different scans are used when generating the combined gum-wax rim model 814.

Two of these scans are of the patient's maxilla and mandibular such that digital 3D representations of these are obtained. The third scan is of the stack with physical models of the gums and the wax rims arranged according to the patient's occlusion.

In the combined gum-wax rim model the portion corresponding to the patient's maxilla and mandibular in the digital 3D representation of the stack may be subtracted such that in a visualization of the combined gum-wax rim model 814, the digital 3D representations of the patient's mandibular 828 and maxilla 825 can be seen together with the wax rim portions 824, 827 of the digital 3D representation of the stack.

In some embodiments, the upper and lower wax rims are 3D scanned using e.g. a desktop scanner. The obtained digital 3D representation of the upper wax rim 824 is virtually arranged relative to the digital 3D representation of the maxilla 825 thereby generating an upper combined gum-wax rim model 826 as illustrated in FIG. 8. The obtained digital 3D representation of the lower wax rim 827 is arranged relative to the digital 3D representation of the mandibular 828 thereby generating lower combined gum-wax rim model 829.

The relative arrangement of the gum of the maxillary arch and the occlusal plane can be derived based on the digital 3D representation of the lower wax rim.

The incisal edge of the anterior teeth in the mandibular is located from the lower combined gum-wax rim model 829, and the occlusal plane of the denture can be determined.

For patients where the maxillary anterior teeth extends below the incisal edge of the mandibular anterior teeth, a virtual line representing the incisal edge of the anterior teeth in the maxillary can be defined in relation to the digital 3D representation of the lower wax rim 827. This line could also be defined on the physical wax rim model and identified in the scanning using texture recognition techniques.

The occlusal plane may be derived purely mathematically from the combined gum-wax rim model.

The combined gum-wax rim model can also be visualized together with the virtual teeth models to aid the arrangement of these, for example by indicating to an operator where the occlusal plane is located. Based on this visualization, the position and orientation of the virtual teeth models relative to the digital 3D representation of the patient's gums can be adjusted manually by an operator and/or automatically utilizing computer implemented algorithms.

A screen shot of such visualization is seen in FIG. 9 where virtual teeth models 930 for the denture teeth of a maxillary denture for the patient's upper jaw are virtually arranged in relation to the digital 3D representation of the upper wax rim 924 and the digital 3D representation of the gums of the maxillary arch 925. The digital 3D representations of the upper 924 and lower wax rims 927 are slightly transparent such that the virtual teeth models 930 can be seen through the digital 3D representation of the upper wax rim 924. The digital 3D representation of the gums of the mandibular arch 928 is also seen.

When the upper wax rim is configured to have a labial surface which is shaped according to the patient's lips, the virtual teeth models can be arranged at the corresponding surface of the digital 3D representation of the upper wax rim, i.e. such that the labial surface of the virtual teeth models of the maxillary anterior teeth of the denture are aligned with the labial surface of the upper wax rim.

The virtual teeth models for a mandibular denture can be arranged to have occlusal surfaces which are arranged according to the occlusal plane determined based on the wax-rims.

The virtual teeth models corresponding to the denture teeth of the denture are preferably arranged spatially relative to each other forming anatomically correct composition of high aesthetic quality.

When a final arrangement of the virtual teeth models has been identified, the next step is to determine the gingival part of the denture.

Figure 10:
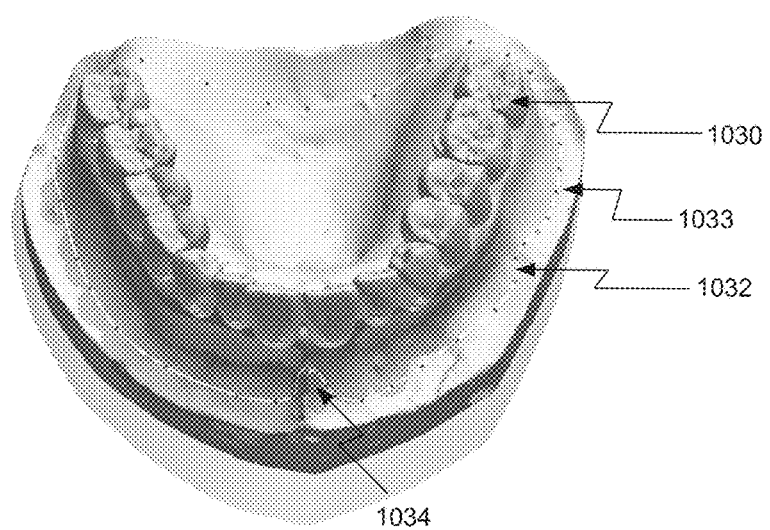
FIG. 10 illustrates how a gingival 3D spline can be defined.

In FIG. 10 is illustrated how a gingival 3D spline 1032 is defined such that it surrounds the virtual teeth models 1030. The gingival 3D spline 1032 follows the sulcus of the gingiva and the patient's ah-line. The gingival 3D spline 1032 can be determined automatically using computer implemented algorithms configured for identifying the bottom/top of the sulcus or by user defined control points 1033 along which the gingival 3D spline is defined. Here the gingival 3D spline is defined to provide that the denture does not contact the sensitive frenum 1034.

Figure 11:
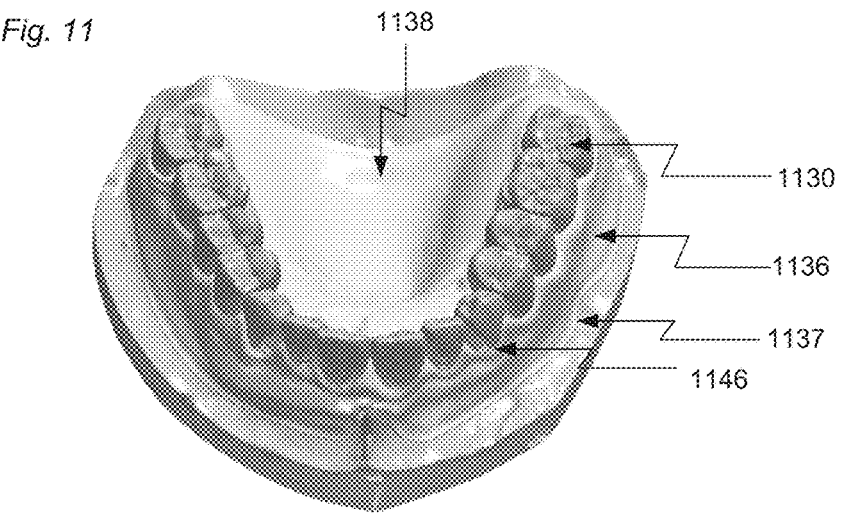
FIG. 11 shows a virtual outer gingival surface of the gingival part of the denture.

FIG. 11 shows a virtual outer gingival surface of the gingival part of the denture. The gingival 3D spline is connected to the virtual teeth models 1130 such that an outer gingival surface or outer surface 1136 of the gingival part of the denture is generated with a boundary or gingival edge 1137 at the patient's sulcus. An anatomically correct appearance of the gingival part can be obtained automatically by e.g. copying the shape of corresponding surfaces in the patient's mouth or manually by the operator using computer implemented modification tools. The modification tools may be configured for virtually adding or removing material to the gingival part of the denture. The gingival part here covers both the patient's alveolar ridge and palette 1138. In FIG. 11, some structure 1146 has been added to the gingival part at the gingival-tooth lines.

Figure 12:
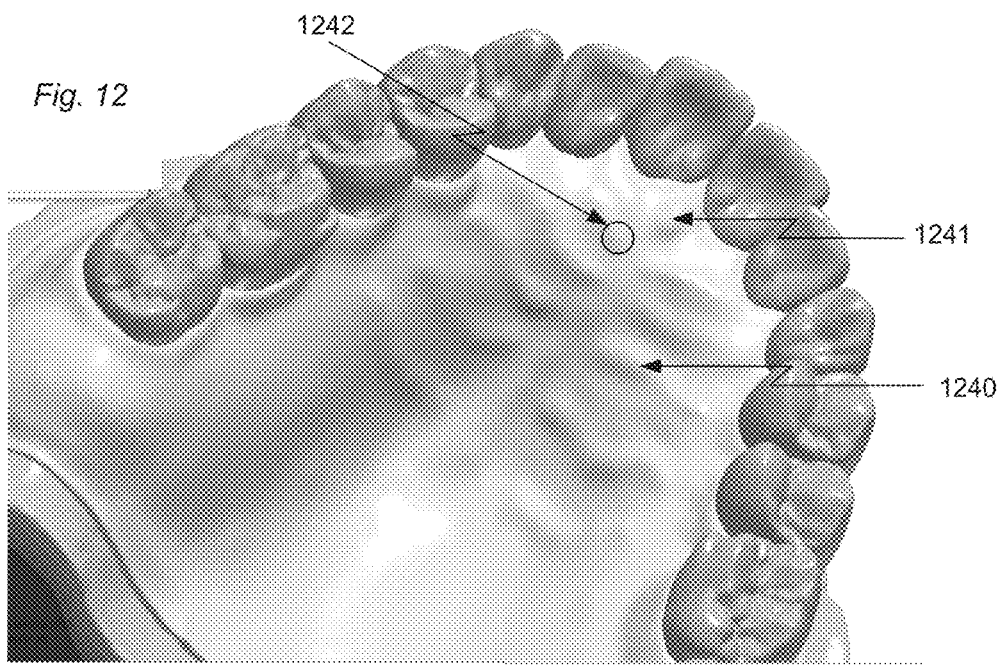
FIG. 12 shows how a virtual rugae structure can be added to the modeled denture.

FIG. 12 shows how a virtual rugae structure can be added to the modeled denture.

In FIG. 12, the patient's rugae 1240 and incisal papilla 1241 is defined using a virtual wax knife (marked with a circle 1242 in the screen shot) as provided in the 3Shape DentalDesigner.

Alternatively and/or additionally the captured alveolar ridge and/or the palette of the patient obtained by the digital 3D representation is used in the design of the denture.

Figure 13:
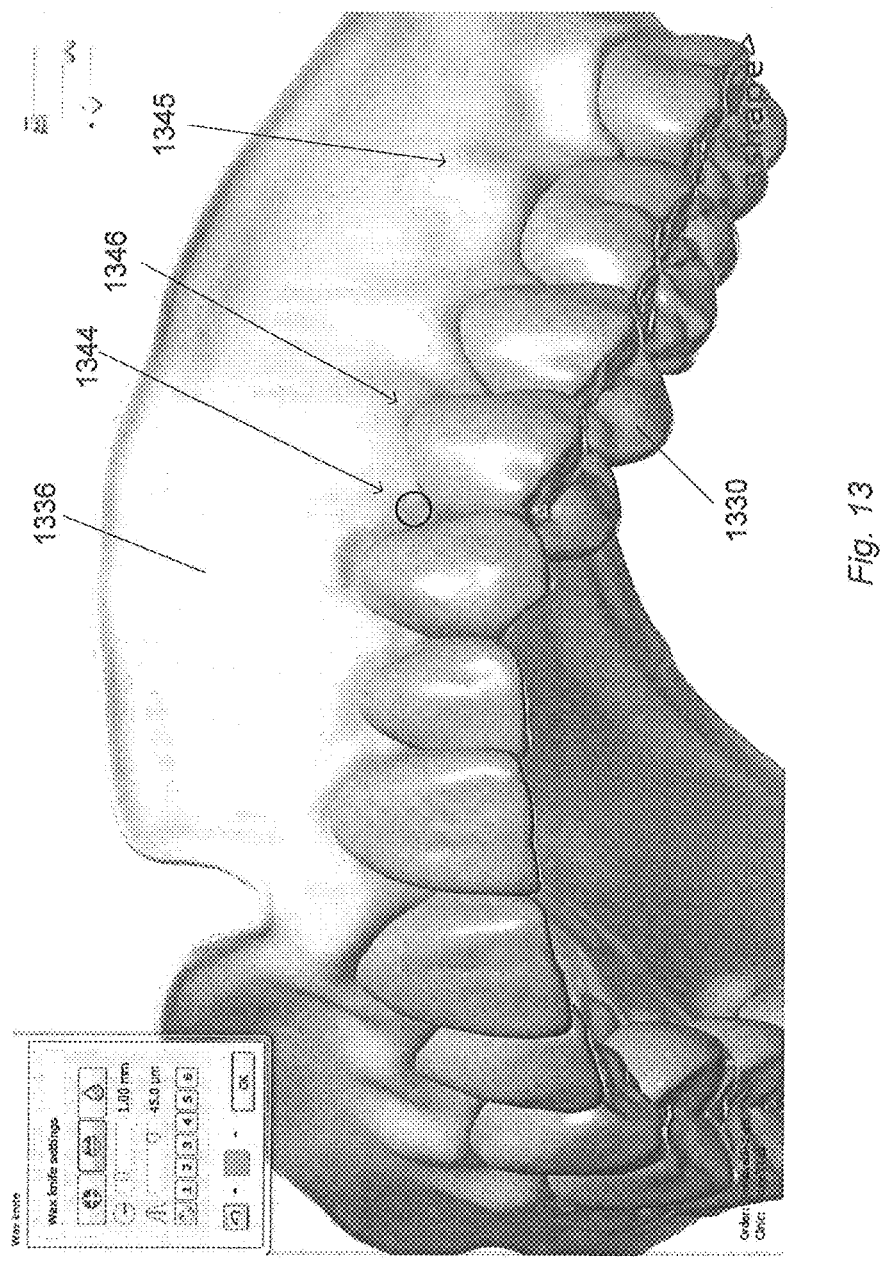
FIG. 13 illustrates how the interproximal gingival can be modified.

FIG. 13 illustrates how the interproximal gingival can be modified.

In FIG. 13, the interproximal gingival is modified using a virtual wax knife 1344 (marked with the circle 1344 in the screen shot), which can for example be performed in the 3Shape DentalDesigner.

In parts of a person's gingival covering the root end of teeth, the root ends normally shape the gingival. In the present figure, the gingival part of the denture has already been shaped according to the shape of the root end of the teeth 1330 by adding virtual root protrusions or cervical protrusions 1345 at the corresponding sections and a marginal gingiva 1346 has been added. This may be done either automatically by providing an offset to the outer surface based on knowledge of the cervical shape of the teeth 1330 or manually using a virtual modifying tool such as the virtual wax-knife.

Figure 14:
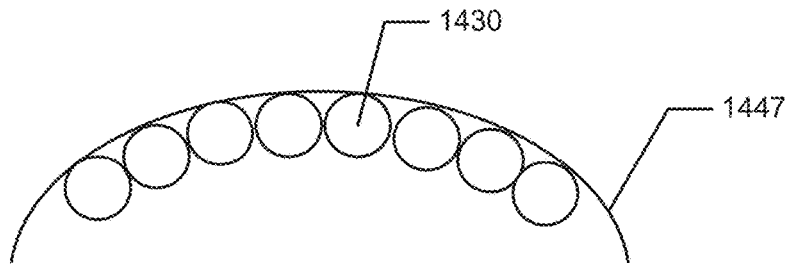
FIG. 14 shows an example of snapping teeth to the occlusal plate.

FIG. 14 shows an example of snapping teeth to the occlusal plate.

FIG. 14 schematically shows the outline of the virtual occlusal plate 1447 with the virtual denture teeth or teeth models 1430 snapped to the rim of the occlusal plate.

Virtually snapped means fixed, attached, maintained, fastened, kept in virtual contact with the occlusal plate etc. Thus even though the operator adjusts the position, orientation and/or shape of the virtual teeth models the teeth models remains in the occlusion given by the occlusal plate due to snapping.

FIGS. 15-24 shows an example of a workflow for digitally designing a denture. It is understood that the different steps of the process may be performed in a different order than shown here, and that the different steps can be left out of the process or be part of a different process.

FIG. 15 shows an example of providing the occlusal plate.

Figure 15A:
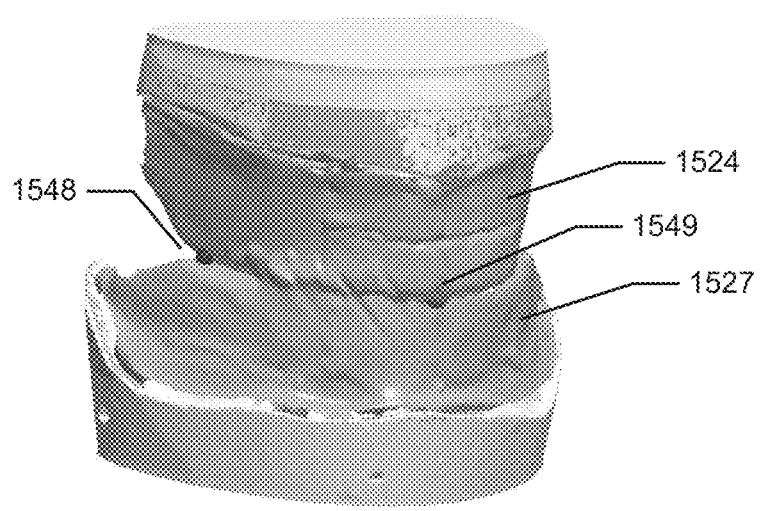
FIG. 15 shows an example of providing an occlusal plate.

FIG. 15*a*) shows an example of placing a number of occlusal points on the wax rim defining the occlusal plate.

The wax rim comprises the upper wax rim 1524 and the lower wax rim 1527. In the figure two occlusal points 1548, 1549 arranged on the wax rim can be seen, however typically three occlusal points will be arranged, so in this case, the third point cannot be seen.

Figure 15B:
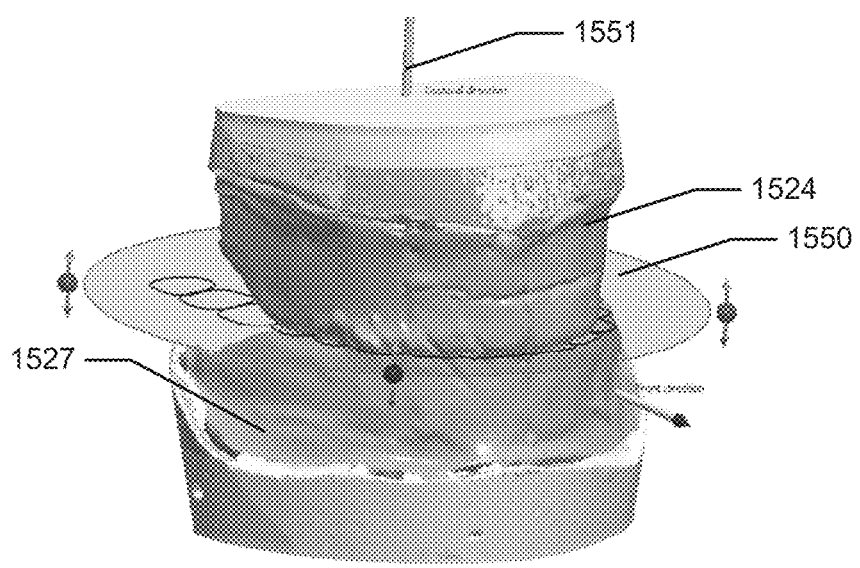

FIG. 15*b*) shows an example where the occlusal plate is shown.

The occlusal plate 1550 is determined or derived based on the occlusal points 1548, 1549.

The line termed "occlusal direction" 1551 and the other arrows on the figure indicates a virtual articulator used for setting up, testing and checking the occlusion.

Thus the occlusal plate can be set up manually or automatically, and the occlusal plate can be manually adjusted if it was set up automatically.

Figure 16:
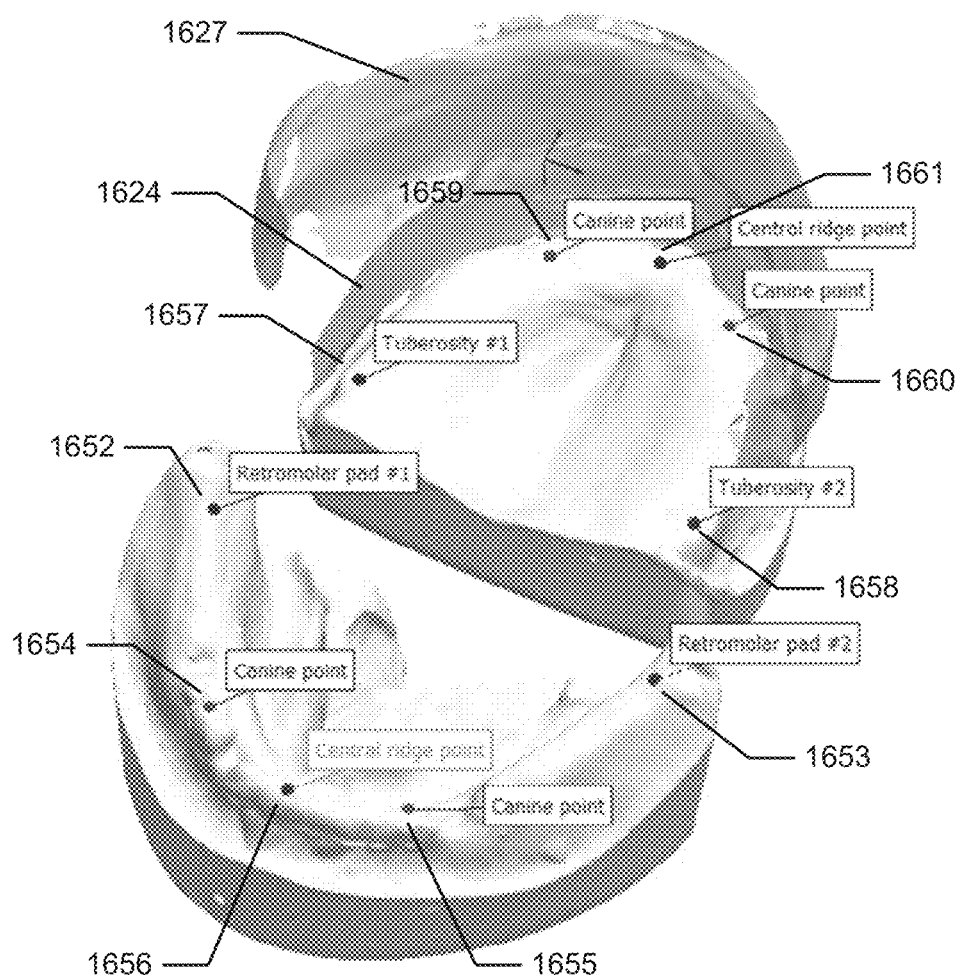
FIG. 16 shows an example of providing a number of characteristic points on the digital 3D representation of the lower jaw and the upper jaw, where the characteristic points determine the placement of teeth models on the jaw(s).

FIG. 16 shows an example of providing a number of characteristic points on the digital 3D representation of the lower jaw and the upper jaw, where the characteristic points determine the placement of teeth models on the jaw(s). The characteristic points may be indicated on the wax rims 1624, 1627 by the dentist in the form of lines marked in the wax rim indicating the midline, which will provide the central ridge points, and/or indicating the canine lines which will provide the canine points. In the wax rim the smile line may also be marked by the dentist indicating the height of the anterior teeth.

Alternatively and/or additionally, the operator may virtually place the characteristic points on the digital 3D representation, or the characteristic points may be automatically placed. The characteristic points may also be placed automatically first and then the operator can adjust them afterwards.

The characteristic points can be placed based on certain rules for placement. In FIG. 16 the characteristic points on the lower jaw are the retromolar pad #1 1652, the retromolar pad #2 1653, the first canine point 1654, the second canine point 1655, and the central ridge point 1656.

The characteristic points on the upper jaw in FIG. 16 are the tuberosity #1 1657, the tuberosity #2 1658, the first canine point 1659, the second canine point 1660, and the central ridge point 1661.

FIG. 17 shows an example of generating the boundary or edge for the upper jaw part of a denture.

Figure 17A:
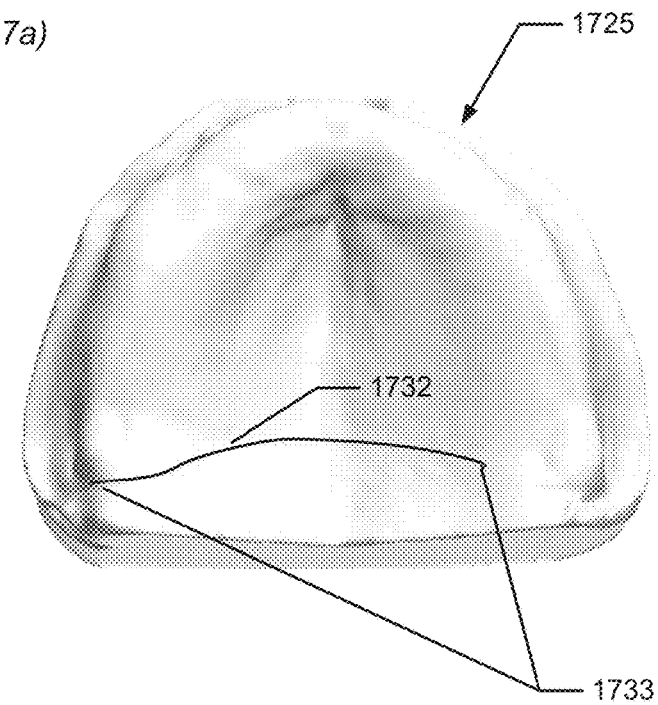
FIG. 17 shows an example of generating the boundary or edge for the upper jaw part of a denture.

FIG. 17*a*) shows an example where the user or operator has virtually marked the outline or gingival 3D spline 1732 of the denture on the digital 3D representation or digital 3D representation of the upper jaw 1725. The outline or gingival 3D spline 1732 may be generated by means of user defined control points 1733 virtually placed on the digital 3D representation of the upper jaw or by the operator drawing a virtual line. The outline or gingival 3D spline 1732 could also be generated automatically by means of software tools.

Figure 17B:
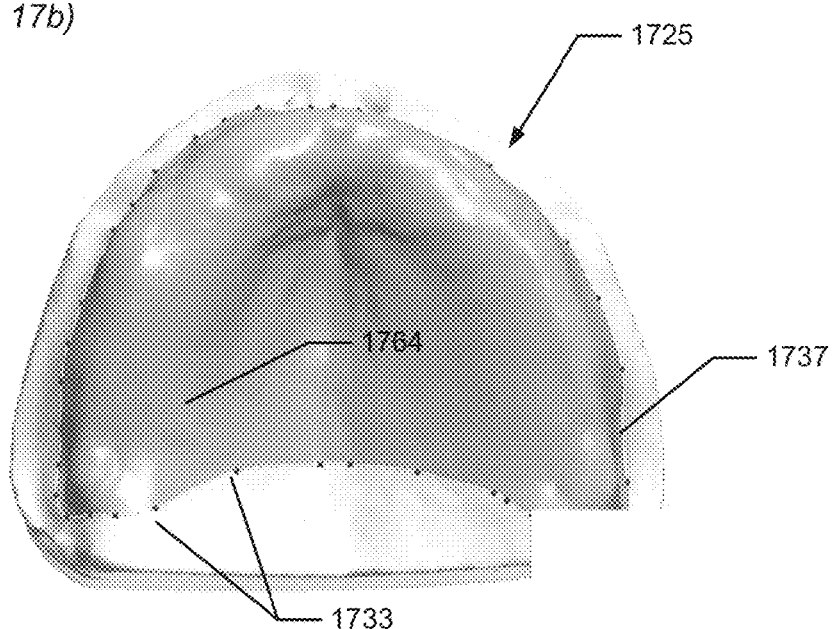

FIG. 17*b*) shows an example where the denture 1764 is virtually shown on the digital 3D representation of the upper jaw 1725. Control points 1733 for the generation of the boundary or gingival edge 1737 are seen. The control points can be adjusted by the operator.

FIG. 18 shows an example of generating the boundary or edge for the lower jaw part of a denture.

Figure 18A:
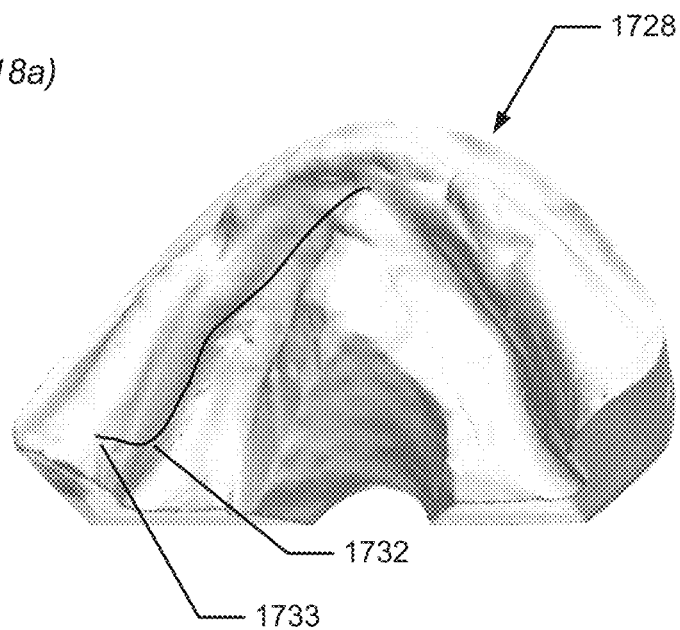
FIG. 18 shows an example of generating the boundary or edge for the lower jaw part of a denture.

FIG. 18*a*) shows an example where the user or operator has virtually marked the outline or gingival 3D spline 1732 of the denture on the digital 3D representation or digital 3D representation of the lower jaw 1728. The outline or gingival 3D spline 1732 may be generated by means of user defined control points 1733 virtually placed on the digital 3D representation of the lower jaw or by the operator drawing a virtual line. The outline or gingival 3D spline 1732 could also be generated automatically by means of software tools.

Figure 18B:
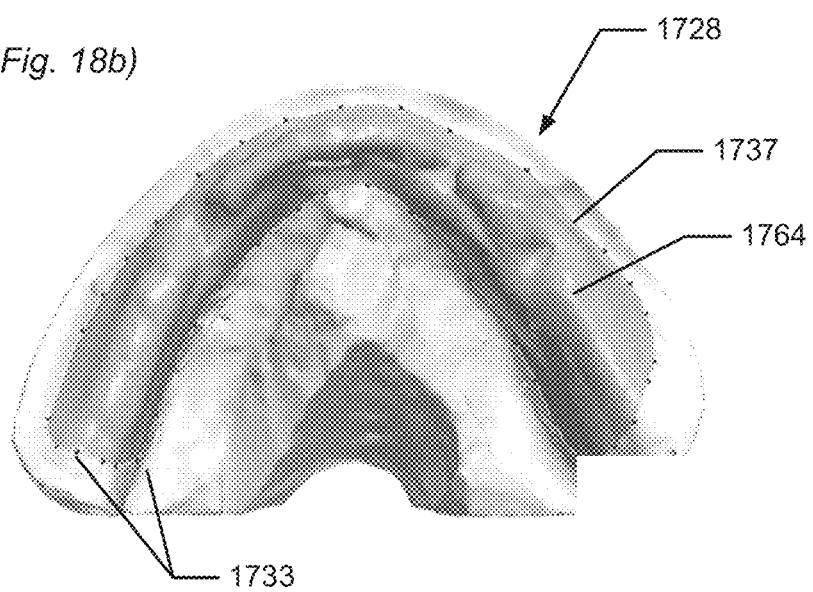

FIG. 18*b*) shows an example where the denture 1764 is virtually shown on the digital 3D representation of the lower jaw 1728. Control points 1733 for the generation of the boundary or gingival edge 1737 are seen. The control points can be adjusted by the operator.

Figure 19:
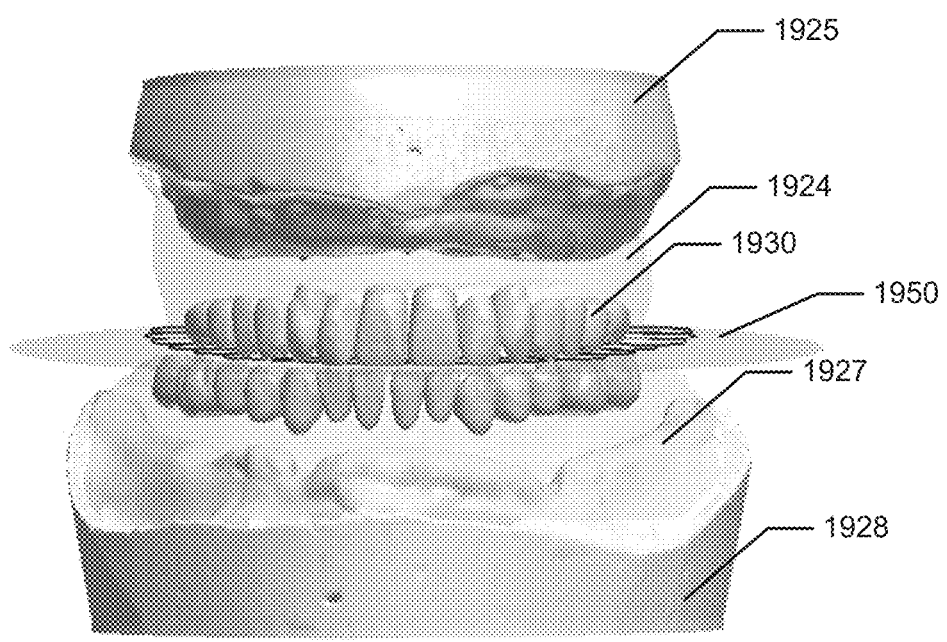
FIG. 19 shows an example of a virtual initial arrangement of the virtual denture teeth.

FIG. 19 shows an example of a virtual initial arrangement of the virtual denture teeth 1930 relative to the virtual 3D representations of the jaws 1925, 1928, and the wax rims 1924, 1927, and the occlusal plane 1950.

The teeth models may be automatically placed initially and the operator may then afterwards adjust the relative positions. The teeth models shown in FIG. 19 are maybe not arranged in occlusion, aligned or arranged correct relative to each other, for example is the interproximal gap between the lower centrals too big. The operator will ensure to adjust this in subsequent steps, either automatically or manually.

FIG. 20 shows examples of the software tools available for digitally designing and adjusting the denture design.

Figure 20A:
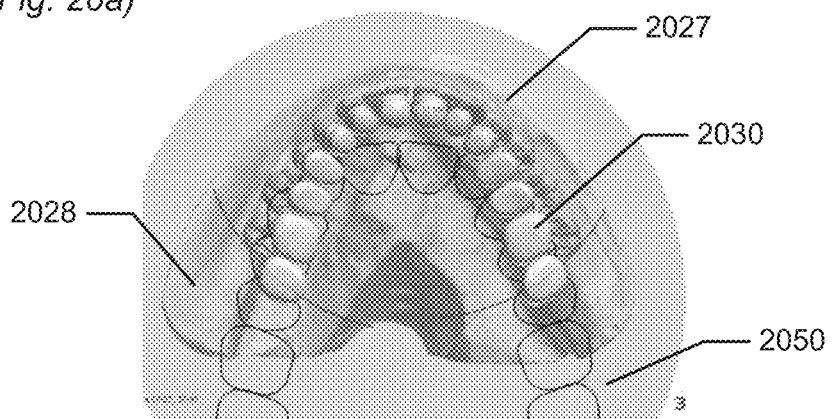
FIG. 20 shows examples of the software tools available for digitally designing and adjusting the denture design.

FIG. 20*a*) shows an example of arc transformation. If the predefined areas 2065 for the teeth on the occlusal plate 2050 do not fit the arc of the digital 3D representation of the gum 2028 and/or the digital 3D representation of the wax rim 2027 and/or the initial positions of the virtual teeth models 2030, then the arc of the indicated teeth 2065 on the occlusal plate 2050 can be adjusted to fit the digital 3D representation of the gum 2028 and/or the digital 3D representation of the wax rim 2027 and the virtual teeth models 2030, or the arc of the virtual teeth models 2030 can be adjusted to fit the arc of the teeth on the occlusal plate 2050 and/or the digital 3D representation of the gum 2028 and/or the digital 3D representation of the wax rim 2027.

Figure 20B:
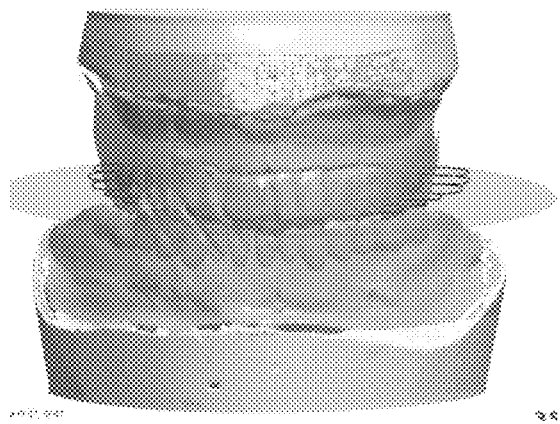

FIG. 20*b*) shows an example of wax rim reference.

Figure 20C:
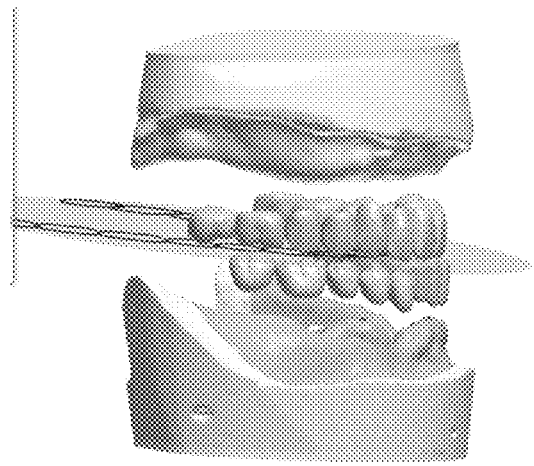

FIG. 20*c*) shows an example of individual transformation.

FIG. 21 shows examples of generating the virtual gingival of the denture.

Figure 21A:
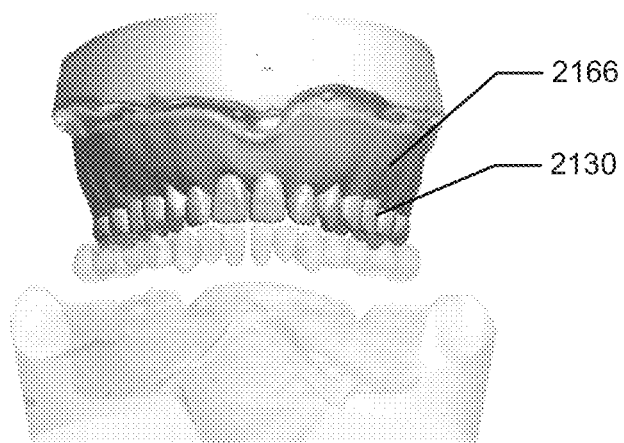
FIG. 21 shows examples of generating the virtual gingival of the denture.

FIG. 21*a*) shows an example of the generated gingival for the upper part of the denture. The virtual outer gingival surface 2166 may be generated by connecting the gingival-tooth lines of the teeth models 2130 with the generated gingival edge, see FIG. 17. Furthermore, material settings, such the base thickness and the relief, may also be used in generating the virtual outer gingival surface 2166.

Figure 21B:
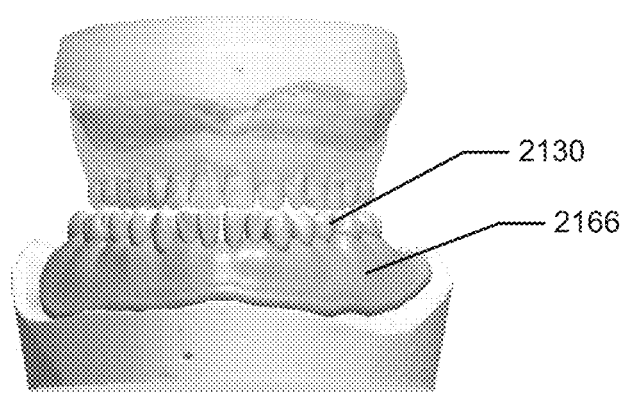

FIG. 21*b*) shows an example of the generated gingival for the lower part of the denture. The virtual outer gingival surface 2166 may be generated by connecting the gingival-tooth lines of the teeth models 2130 with the generated gingival edge, see FIG. 17.

Furthermore, material settings, such the base thickness and the relief, may also be used in generating the virtual outer gingival surfaces 2166 for the lower and upper part of the denture.

FIG. 22 shows examples of inspecting the digital design of the denture.

Figure 22A:
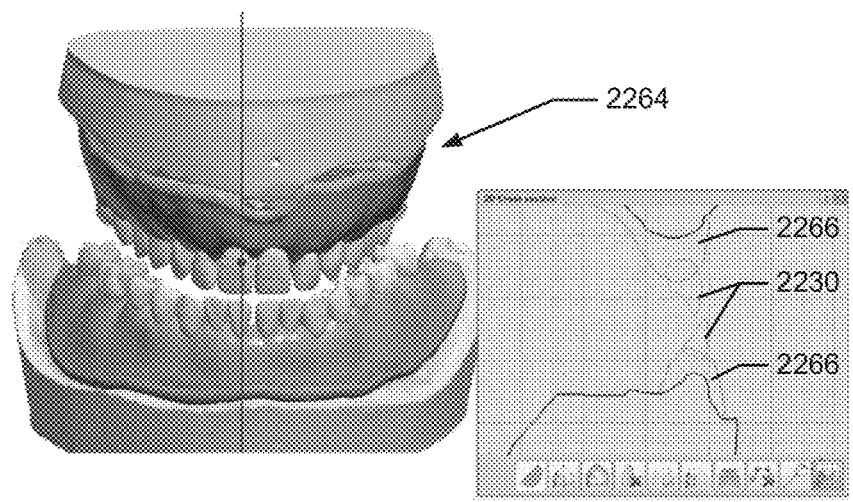
FIG. 22 shows examples of inspecting the digital design of the denture.
Figure 22B:
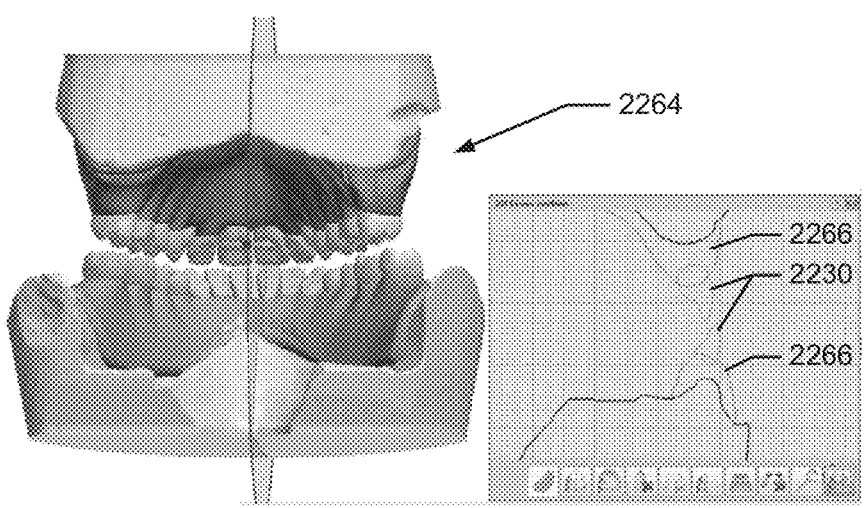

The design of the denture can be viewed from different viewpoints, such as from the front, see FIG. 22*a*) and from the back, see FIG. 22*b*). A 2D cross section of the denture design can be made anywhere on the denture. The inserts in the lower right corners of the FIGS. 22*a*) and 22*b*) show a 2D cross section view of the gum, the gingival part and the virtual teeth models of the denture as seen in a plane which is parallel to the sagittal plane of the patient. In the 2D cross section view, the operator can for example see how far into the gingiva 2066 the model teeth 2030 reach.

FIG. 23 shows an example of designing features on the gingival part of the denture.

Figure 23A:
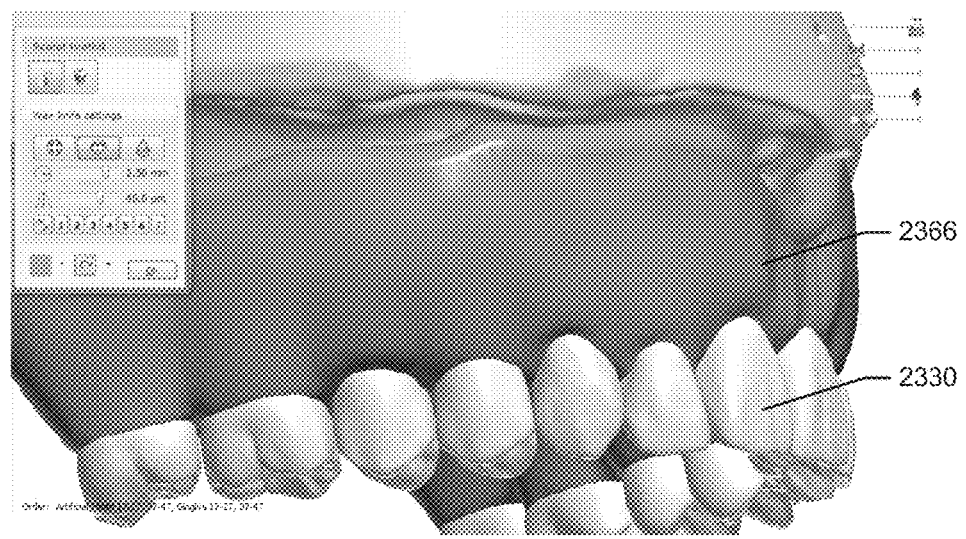
FIG. 23 shows an example of designing features on the gingival part of the denture.

FIG. 23*a*) shows the maxillary before designing features.

Figure 23B:
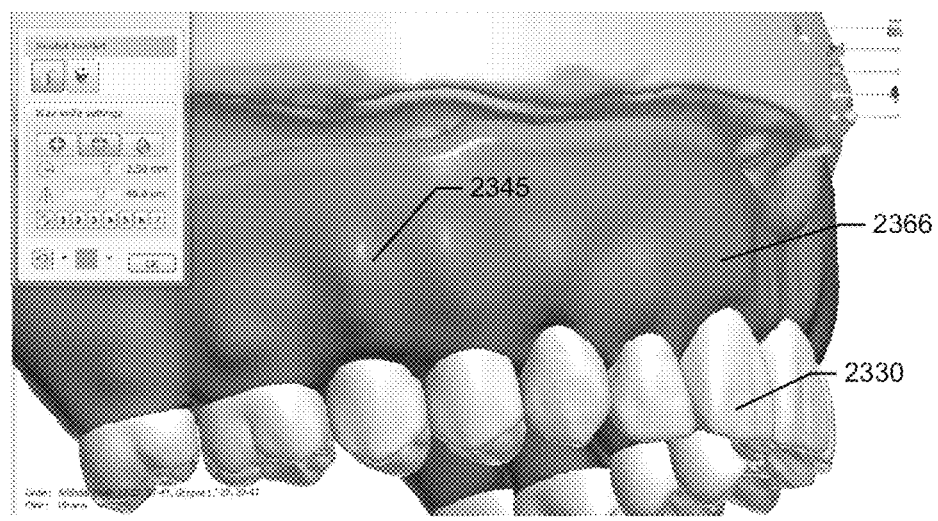

FIG. 23*b*) shows the maxillary when virtual root protrusions or cervical protrusions 2345 have been added at the roots ends of the virtual teeth 2330 on the gingiva 2366.

Figure 23C:
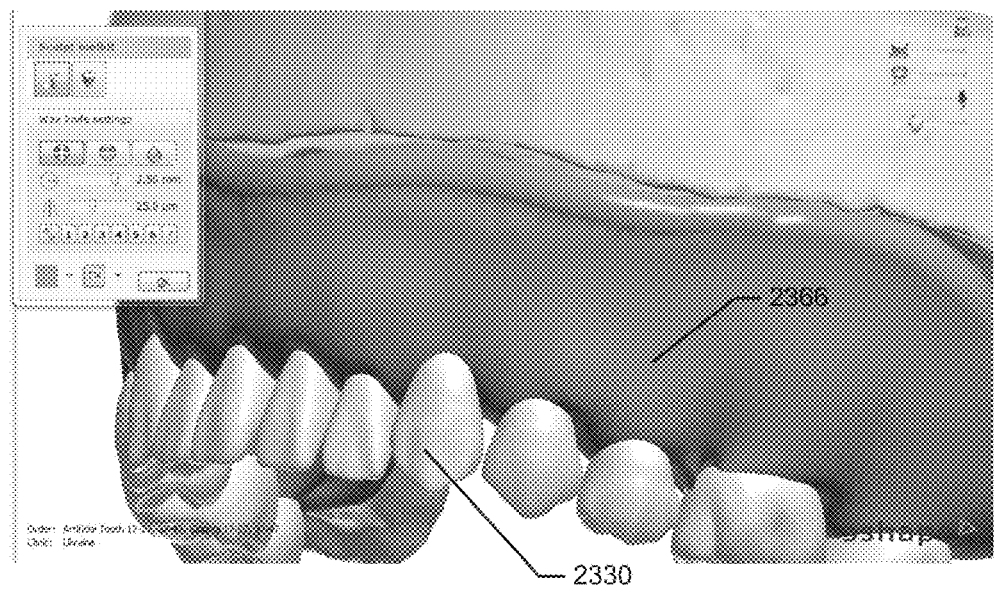
Figure 23D:
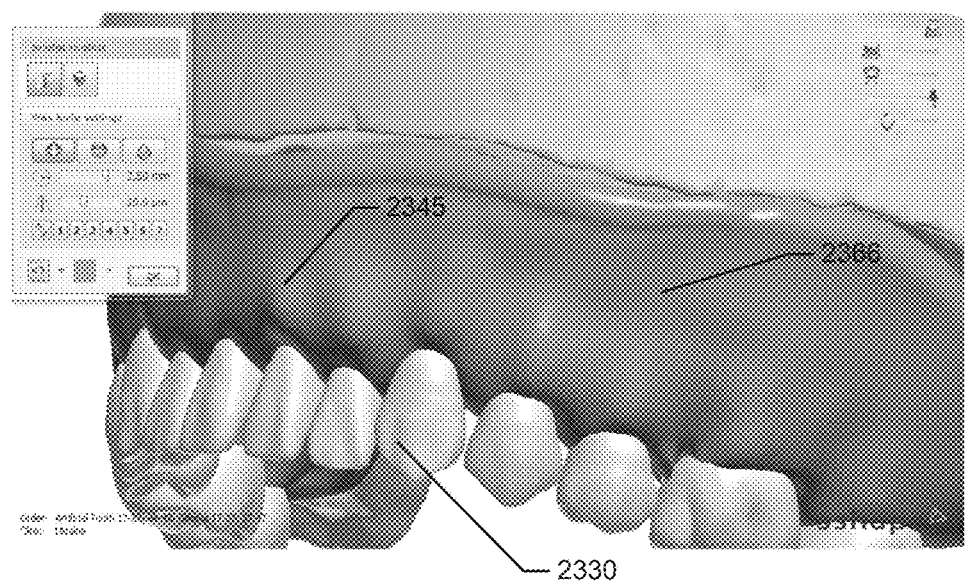

FIG. 23*c*) shows the mandible before designing features.

FIG. 23*b*) shows the mandible when virtual root protrusions or cervical protrusions 2345 have been added at the roots ends of the virtual teeth 2330 on the gingiva 2366.

Figure 24:
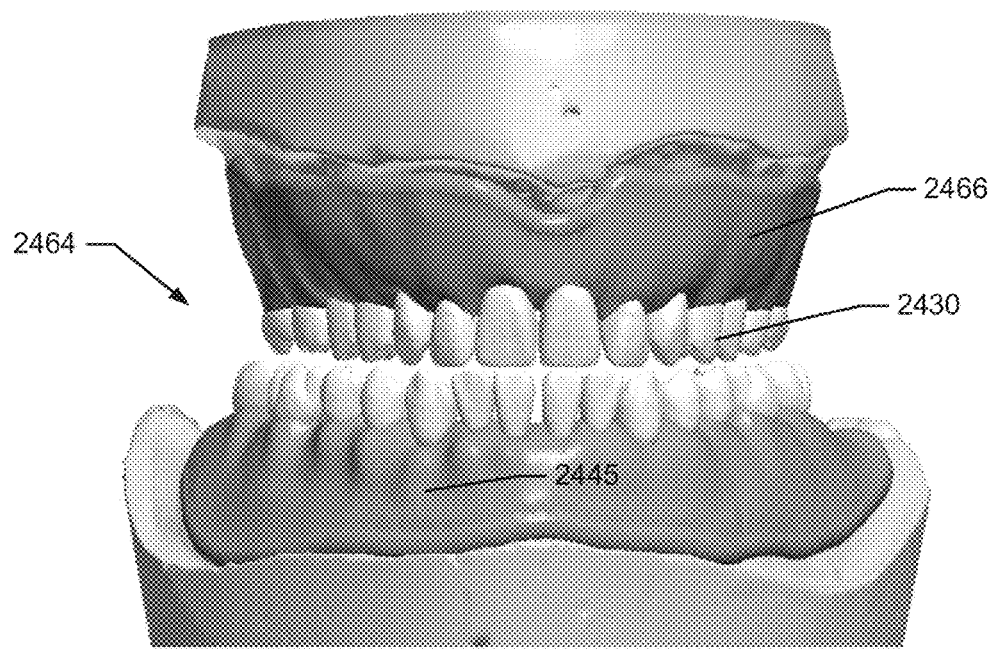
FIG. 24 shows an example of a final design of a denture.

FIG. 24 shows an example of a final design of a denture.

The final design of the denture 2464 comprises virtual model teeth 2430 in the upper and lower jaw, and virtual gingival 2466 comprising virtual root protrusions or cervical protrusions 2445.

The denture design is now ready to be manufactured to produce a physical denture for the patient's mouth.

FIG. 25 shows examples of virtual occlusal plates.

Figure 25A:
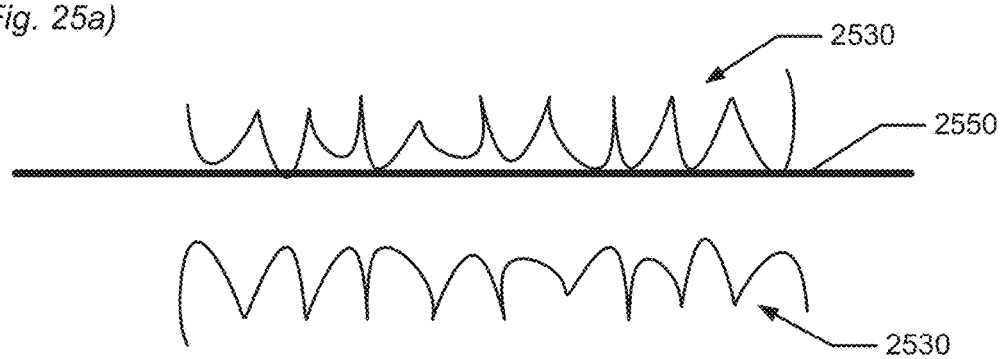
FIG. 25 shows examples of virtual occlusal plates.

FIG. 25*a*) shows an example of a straight occlusal plate 2550 virtually arranged between upper and lower virtual teeth 2530.

Figure 25B:
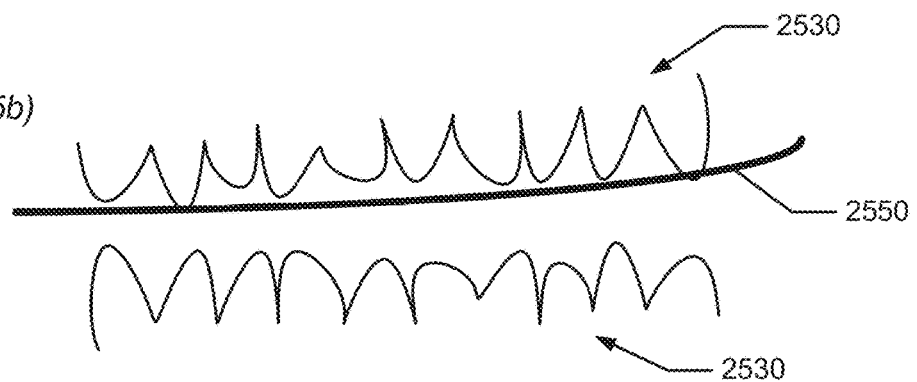

FIG. 25*b*) shows an example of a curved occlusal plate 2550 virtually arranged between upper and lower virtual teeth 2530.

FIG. 26 shows schematic examples of designing the virtual outer gingival surface.

Figure 26A:
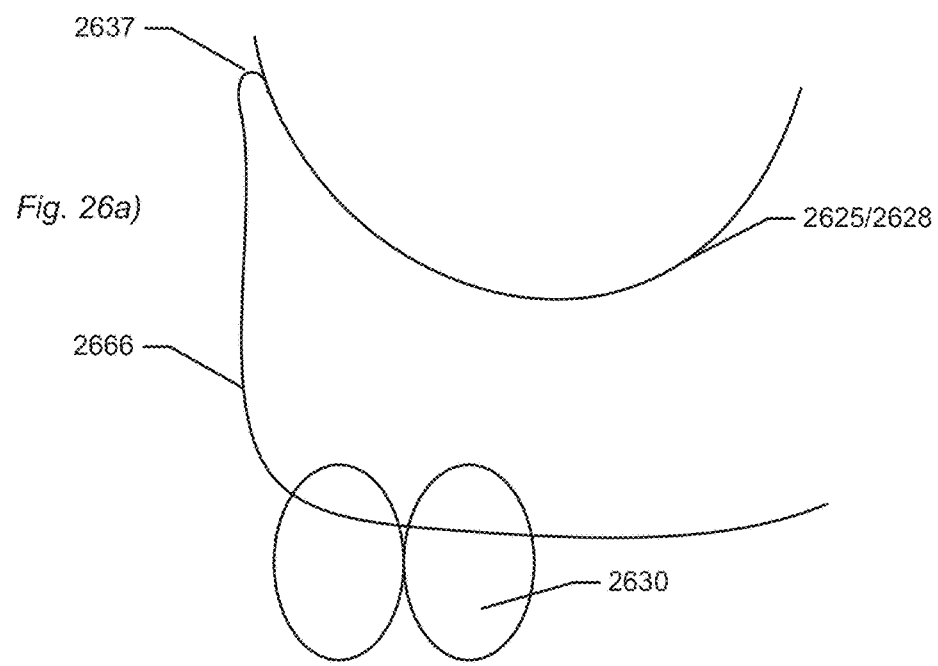
FIG. 26 shows schematic examples of designing the virtual outer gingival surface.

FIG. 26a) shows an example where the outer gingival surface 2666 of the denture is virtually designed to be rounded off at the gingival edges or boundaries 2637. The figure also shows virtual model teeth 2630 and the upper or lower jaw 2625/2628.

Figure 26B:
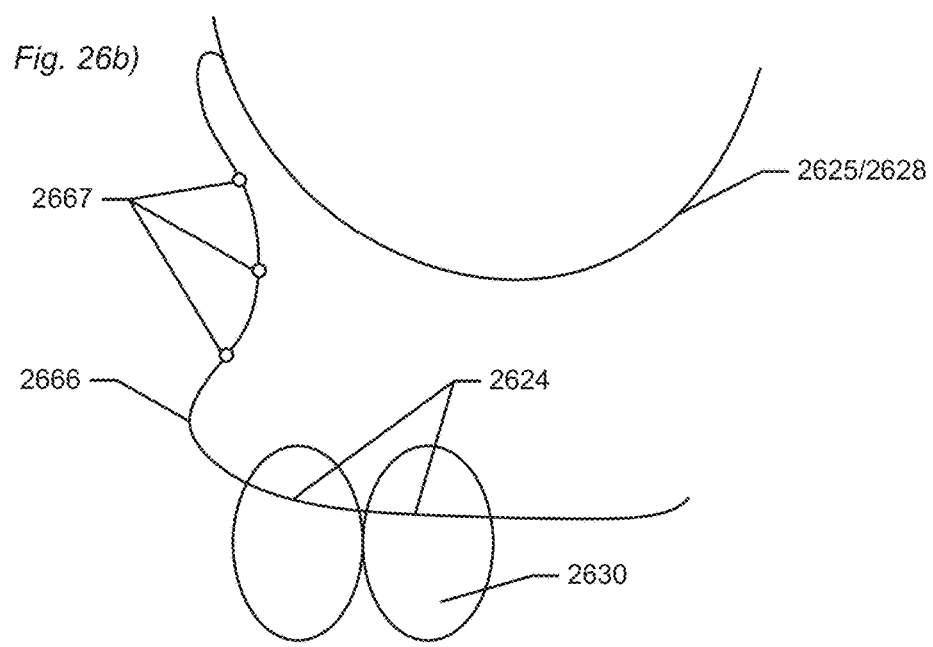

FIG. 26b) shows an example of adjustment of the virtual outer gingival surface 2666. The adjustment is performed by pulling in one or more control points 2667 arranged on the virtual outer gingival surface 2666. The virtual outer gingival surface 2666 is adjusted such that it curves inwards between the patient's gums 2625/2628 and the gingival-tooth line 2624 on the teeth models 2620.

FIG. 27 shows schematic examples of designing the part of the denture for the upper jaw.

Figure 27A:
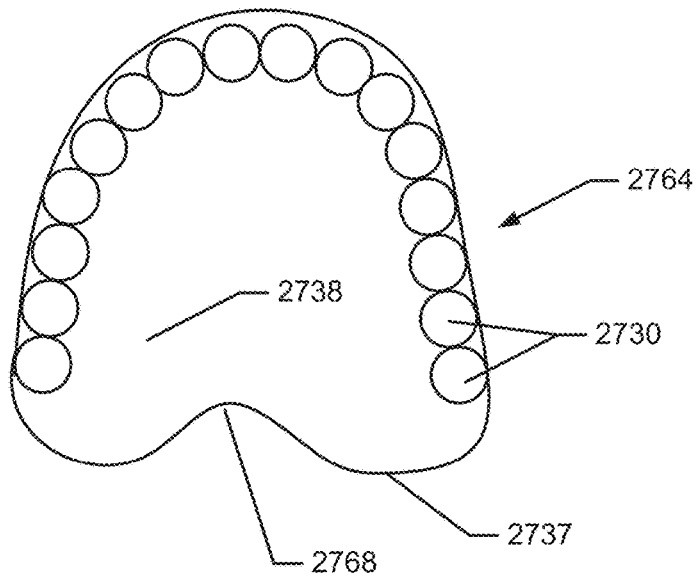
FIG. 27 shows schematic examples of designing the part of the denture for the upper jaw.

FIG. 27a) shows an example of the upper part of a denture 2764. An indention 2768 in the center of the palate or palette area 2738 at the gingival edge or boundary 2737 of the denture is virtually designed, since two salivary glands have their outlet at the palate in the human mouth and the denture should be designed not to cover these glands.

Figure 27B:
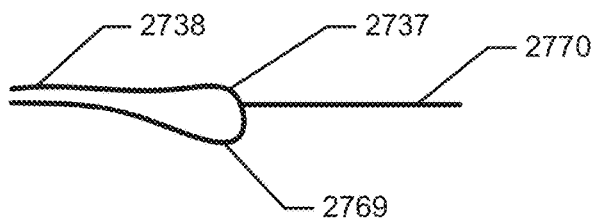

FIG. 27b) shows an example of virtually designing a protrusion 2769 on the gingival edge or boundary 2737 of the palate or palette area 2738 of the denture. The function of the protrusion 2769 is to create a vacuum under the palate or palette area 2738 of the upper jaw denture, whereby the upper denture part will be sucked to the patient's own palate 2770.

Figure 28:
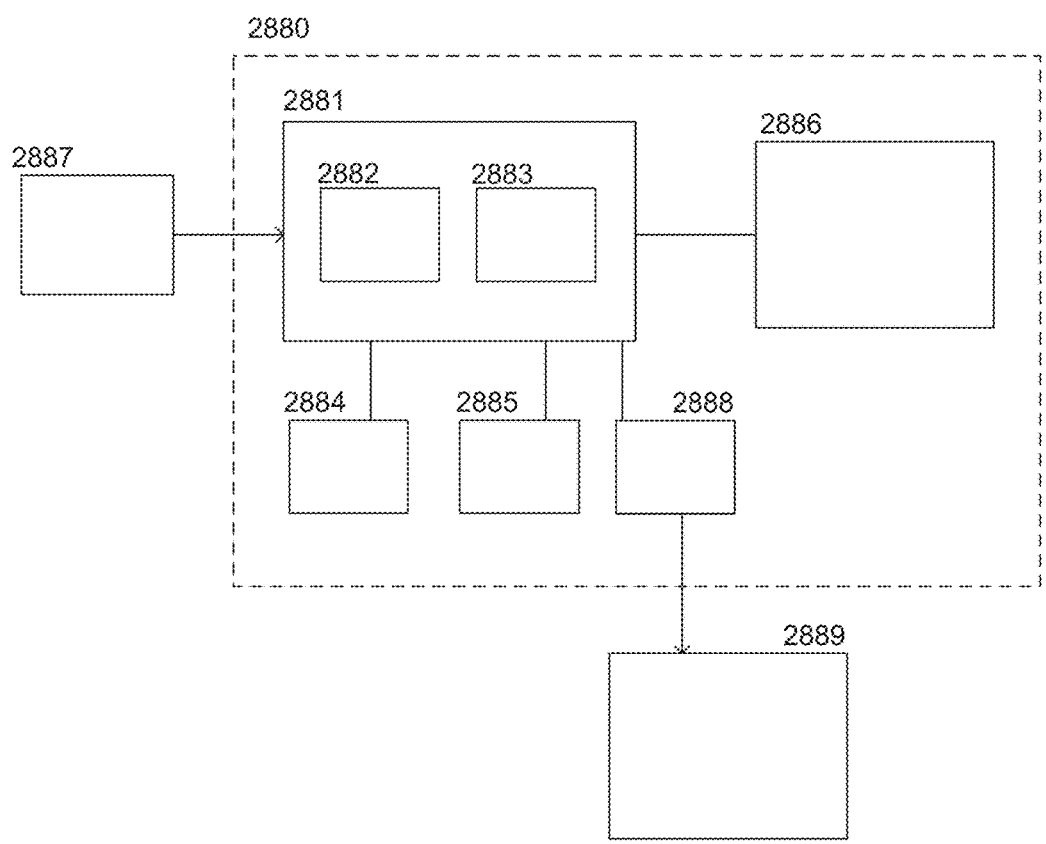
FIG. 28 shows a schematic of a system according to an embodiment of the present invention.

FIG. 28 shows a schematic of a system according to an embodiment of the present invention. The system 2880 comprises a computer device 2881 comprising a computer readable medium 2882 and a data processing unit 2883. The system further comprises a visual display unit 2886, a computer keyboard 2884 and a computer mouse 2885 for entering data and activating virtual buttons visualized on the visual display unit 2886. The visual display unit 2886 can be a computer screen. The computer device 2881 is capable of receiving a digital 3D representation of the patient's gum from a scanning device 2887, such as the TRIOS intra-oral scanner manufactured by 3shape A/S, or capable of receiving scan data from such a scanning device and forming a digital 3D representation of the patient's gum based on such scan data. The received or formed digital 3D representation can be stored in the computer readable medium 2882 and provided to the data processing unit 2883. The data processing unit 2883 is configured for obtaining virtual teeth models corresponding to the denture teeth, for virtually arranging the virtual teeth models in relation to the digital 3D representation of the patient's gum, and for generating a virtual outer gingival surface of the gingival part of the denture using the method according to any of the embodiments. In the virtually arranging the virtual teeth models in relation to the digital 3D representation of the patient's gum and generating a virtual outer gingival surface of the gingival part of the denture, one or more options can be presented to the operator, such as whether to move a one or more teeth one by one or as a group. Other options can relate to numerical values for e.g. thickness of the gingival part of the denture. The options can be presented in a user interface visualized on the visual display unit 2886.

The system comprises a unit 2888 for transmitting the virtual digital 3D representation or a 3D model formed from this to e.g. a computer aided manufacturing (CAM) device 2889 for manufacturing the dental restoration or to another computer system e.g. located at a milling center where the dental restoration is manufactured. The unit for transmitting the virtual 3D model can be a wired or a wireless connection.

The scanning of the patient's gums using the scanning device 2887 can be performed at a dentist while the digitally designing of the denture is performed at a dental laboratory. In such cases the digital 3D representation or a 3D model of the patient's gum can be provided via an internet connection between the dentist and the dental laboratory.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

Embodiments

1. A method for modeling a digital design of a denture for a patient, said denture comprising a gingival part and a teeth part comprising a set of denture teeth, where the method comprises:
   obtaining a digital 3D representation of the patient's gum;
   obtaining virtual teeth models corresponding to the denture teeth;
   virtually arranging the virtual teeth models in relation to the digital 3D representation of the patient's gum; and
   generating a virtual outer gingival surface of the gingival part of the denture.

2. The method according to embodiment 1, wherein the part of the patient's gum(s) that are scanned when obtaining the digital 3D representation relates to at least the alveolar ridge and/or the palette at which the denture is to be arranged.

3. The method according to any of the previous embodiments, wherein the obtained digital 3D representation of the patient's gum relates to the patient's upper jaw and/or to the patient's lower jaw.

4. The method according to any of the previous embodiments, wherein the alveolar ridge and/or the palette of the obtained digital 3D representation is used in the design of the denture.

5. The method according to any of the previous embodiments, wherein the method comprises obtaining the patient's occlusal plane by means of an electronic facebow or a mechanical facebow.

6. The method according to any of the previous embodiments, wherein the method comprises obtaining the patient's occlusal plane by means of physical impressions of the patient's upper and lower gums and/or by one or more measurements of the patient's face and mouth.

7. The method according to any of the previous embodiments, wherein the method comprises:
    obtaining a 3D digital representation of the physical impression of the patient's upper jaw;
    obtaining a 3D digital representation of the physical impression of the patient's lower jaw; and
    obtaining a 3D digital representation of the physical impressions of the patient's upper jaw and lower jaw arranged together.

8. The method according to any of the previous embodiments, wherein the patient's upper jaw and lower jaw are arranged together in occlusion.

9. The method according to any of the previous embodiments, wherein the method comprises performing measurements of the patient's face and mouth.

10. The method according to any of the previous embodiments, wherein the method comprises providing a straight occlusal plate.

11. The method according to any of the previous embodiments, wherein the method comprises providing a curved occlusal plate.

12. The method according to any of the previous embodiments, wherein the method comprises selecting a virtual occlusal plate for modeling the patient's denture.

13. The method according to any of the previous embodiments, wherein the method comprises forming an upper wax rim for the patient's maxillary arch and/or forming a lower wax rim for the patient's mandibular arch.

14. The method according to any of the previous embodiments, wherein the method comprises obtaining a digital 3D representation of the lower wax rim and/or obtaining a digital 3D representation of the upper wax rim.

15. The method according to any of the previous embodiments, wherein the method comprises virtually arranging the teeth models relative to the digital 3D representations of the upper and/or lower wax rim.

16. The method according to any of the previous embodiments, wherein the method comprises providing a virtual occlusal plate relative to digital 3D representations of the wax rims and/or the digital 3D representation of the patient's gums, and virtually arranging the virtual teeth models relative to the virtual occlusal plate.

17. The method according to any of the previous embodiments, wherein the virtual teeth models in the lower jaw or the upper jaw are arranged in occlusion by means of a virtual occlusal plate, and the virtual teeth models are then arranged in the upper jaw or lower jaw, respectively, relative to the already arranged teeth models in the antagonist jaw.

18. The method according to any of the previous embodiments, wherein the virtual teeth models are virtually snapped to the occlusal plate.

19. The method according to any of the previous embodiments, wherein method comprises adjusting the curvature of the occlusal plate is to provide that the occlusal plate substantially follows the curvature of the patient's jaws.

20. The method according to any of the previous embodiments, wherein the method comprises adjusting the curvature of the occlusal plate by virtually pulling in one or more control points of the occlusal plate.

21. The method according to any of the previous embodiments, wherein the method comprises selecting virtual teeth models from a virtual library comprising virtual sets of teeth models, such as selecting a set of teeth models from a virtual library.

22. The method according to any of the previous embodiments, wherein the different sets of teeth models from the virtual library have different arrangements of the teeth models.

23. The method according to any of the previous embodiments, wherein the different sets of teeth models from the virtual library have different teeth shapes and/or sizes, such as round, square, triangular, short, long, wide and/or narrow.

24. The method according to any of the previous embodiments, wherein a set of teeth models for the lower jaw and/or a set of teeth models for the upper jaw is/are selected.

25. The method according to any of the previous embodiments, wherein the set of teeth models for the lower jaw and the set of teeth models for the upper jaw are a pair fitting together and arranged in occlusion.

26. The method according to any of the previous embodiments, wherein the sets of teeth models in the library are provided by 3D scanning physical dentures comprising the physical versions of the teeth models arranged in the sets.

27. The method according to any of the previous embodiments, wherein the virtual teeth models are aligned relative to the sets of teeth models.

28. The method according to any of the previous embodiments, wherein teeth models from different sets of teeth models are combined for the denture.

29. The method according to any of the previous embodiments, wherein the method comprises virtually adjusting the position, shape and/or orientation of one or more of the teeth models in the sets.

30. The method according to any of the previous embodiments, wherein virtually adjusting the position, shape and/or orientation of one or more of the teeth models in the sets comprises:
    translating a tooth model;
    rotating a tooth model; and/or
    morphing a tooth model.

31. The method according to any of the previous embodiments, wherein the occlusion of the set of teeth for the lower jaw and the set of teeth for upper jaw is maintained, when the position, shape and/or orientation of one or more of the teeth models in the set(s) is adjusted.

32. The method according to any of the previous embodiments, wherein the interproximal contact between neighbor teeth models is maintained, when the position, shape and/or orientation of one or more of the teeth models in the set(s) is adjusted.

33. The method according to any of the previous embodiments, wherein the method comprises virtually adjusting the position, shape and/or orientation for a group of teeth models.

34. The method according to any of the previous embodiments, wherein the method comprises replacing one or more teeth models in the selected set of teeth with teeth models from another set of teeth from the library.

35. The method according to any of the previous embodiments, wherein the method comprises virtually designing one or more of the teeth for the denture.

36. The method according to any of the previous embodiments, wherein the method comprises providing a number of characteristic points on the digital 3D representation of the lower jaw and/or on the digital 3D representation of the upper jaw.

37. The method according to any of the previous embodiments, where the characteristic points determine the placement of teeth models on the jaw(s).

38. The method according to any of the previous embodiments, wherein the virtual set of teeth models selected from a virtual library of teeth models is selected based on the relative positions of the characteristic points.

39. The method according to any of the previous embodiments, wherein providing the number of characteristic points comprises that an operator virtually places the characteristic points.

40. The method according to any of the previous embodiments, wherein providing the number of characteristic points comprises that the characteristic points are automatically placed.

41. The method according to any of the previous embodiments, wherein the characteristic points on the lower jaw comprise one or more of:
 a retromolar pad #1;
 a retromolar pad #2;
 a first canine point;
 a second canine point; and
 a central ridge point.

42. The method according to any of the previous embodiments, wherein the characteristic points on the upper jaw comprise one or more of:
 tuberosity #1;
 tuberosity #2;
 a first canine point;
 a second canine point; and
 a central ridge point.

43. The method according to any of the previous embodiments, wherein a try-in denture is printed when the denture has been designed.

44. The method according to any of the previous embodiments, wherein a light-curable material is used for printing the try-in denture.

45. The method according to any of the previous embodiments, wherein the printed try-in denture is 3D scanned after a potential adjustment of the teeth in the try-in denture.

46. The method according to any of the previous embodiments, wherein a try-in denture is manufactured in wax, the wax try-in denture is 3D scanned, and based on the 3D scan of the wax try-in denture an acrylic final denture is printed.

47. The method according to any of the previous embodiments, wherein the method comprises defining a gingival 3D spline marking an outer boundary curve of the denture directly on the digital 3D representation of the patient's gum when this is visualized on a computer screen.

48. The method according to any of the previous embodiments, wherein the method comprises defining a gingival 3D spline in relation to the digital 3D representation of the patient's gum.

49. The method according to any of the previous embodiments, wherein the method comprises virtually arranging the virtual teeth models relative to the gingival part of the denture.

50. The method according to any of the previous embodiments, wherein part of the gingival 3D spline is arranged at the sulcus of the patient's gingival.

51. The method according to any of the previous embodiments, wherein part of the gingival 3D spline is arranged at the patient's ah-line 52. The method according to any of the previous embodiments, wherein the virtual outer gingival surface is configured for connecting the gingival 3D spline and the virtual teeth models.

53. The method according to any of the previous embodiments, wherein gingival-tooth lines are defined for said virtual teeth models and wherein the method comprises connecting the virtual outer gingival surface to the gingival-tooth lines on the virtual teeth models.

54. The method according to any of the previous embodiments, wherein the method comprises extending the virtual outer gingival surface into the interproximal gap between the teeth models.

55. The method according to any of the previous embodiments, wherein said virtual outer gingival surface is generated in least in part by an offset of a corresponding portion of the digital 3D representation of the patient's gum.

56. The method according to any of the previous embodiments, wherein said virtual outer gingival surface is generated at least in part by a loofting process.

57. The method according to any of the previous embodiments, wherein at least part of the virtual outer gingival surface is shaped to resemble the corresponding surfaces in the patient's natural gum.

58. The method according to any of the previous embodiments, wherein at least part of the shape of the virtual outer gingival surface is selected from a gingival library.

59. The method according to any of the previous embodiments, wherein at least part of the shape of the virtual outer gingival surface is modified or generated using a virtual free-form sculpt tool.

60. The method according to any of the previous embodiments, wherein said virtual outer gingival surface is generated at least in part by a virtual marginal gingiva.

61. The method according to any of the previous embodiments, wherein the virtual marginal gingiva is arranged at the gingival part of the denture where the gingiva meets the lingual, labial or buccal face of the virtual teeth models.

62. The method according to any of the previous embodiments, wherein generating the virtual outer gingival surface comprises generating the virtual marginal gingiva and connecting the marginal gingiva to the gingival 3D spline.

63. The method according to any of the previous embodiments, wherein generating the virtual outer gingival surface comprises connecting the gingival 3D spline to the virtual teeth models and then generating the marginal gingiva.

64. The method according to any of the previous embodiments, wherein the gingival 3D spline is connected to a gingival-tooth line on the virtual teeth models.

65. The method according to any of the previous embodiments, wherein the virtual outer gingival surface is configured to be adjusted.

66. The method according to any of the previous embodiments, wherein the adjustment is performed by pulling in one or more control points arranged on the virtual outer gingival surface.

67. The method according to any of the previous embodiments, wherein the virtual outer gingival surface is configured to be adjusted such that it curves inwards between the patient's gums and the gingival-tooth line on the teeth models.

68. The method according to any of the previous embodiments, wherein the method comprises virtually designing the outer gingival surface of the denture to be rounded off at the gingival edges or boundaries.

69. The method according to any of the previous embodiments, wherein the method comprises virtually designing the outer gingival surface of the mandible or lower jaw part of the denture to have a size big enough for the tongue to touch and rest on a part of the outer gingival surface.

70. The method according to any of the previous embodiments, wherein the method comprises virtually designing a protrusion on the gingival edge or boundary of the palate or palette area of the denture.

71. The method according to any of the previous embodiments, wherein the method comprises virtually designing an indention in the center of the palate or palette area at the gingival edge or boundary of the denture.

72. The method according to any of the previous embodiments, wherein said virtual outer gingival surface is generated at least in part by one or more virtual cervical protrusions.

73. The method according to any of the previous embodiments, wherein the method comprises identifying an occlusal plane of the denture.

74. The method according to any of the previous embodiments, wherein the method comprises adjusting the bite height.

75. The method according to any of the previous embodiments, wherein the arranged teeth models are virtually snapped to the digital 3D representation of the wax rim.

76. The method according to any of the previous embodiments, wherein the teeth models are automatically arranged in a predefined distance from the digital 3D representation of the wax rim.

77. The method according to any of the previous embodiments, wherein the centerline and/or the midline of the patient's face is recorded or sketched on the wax rims.

78. The method according to any of the previous embodiments, wherein the method comprises obtaining digital 3D representations of both the patient's mandibular gum and maxillary gum.

79. The method according to any of the previous embodiments, wherein the method comprises arranging physical models of the patient's mandibular and maxillary and the corresponding lower and upper wax rims in a stack according to their relative position in occlusion, and obtaining a digital 3D representation of this stack.

80. The method according to any of the previous embodiments, wherein the method comprises virtually aligning the digital 3D representations of the patient's mandibular and maxillary gums and the digital 3D representation of the stack, such that a combined gum-wax rim model is generated.

81. The method according to any of the previous embodiments, wherein gum-wax rim models are defined for each of the maxillary and the mandibular.

82. The method according to any of the previous embodiments, wherein the relative arrangement of the gum of the maxillary arch and the occlusal plane is derived.

83. The method according to any of the previous embodiments, wherein the relative arrangement of the gum of the mandibular arch and the occlusal plane is derived.

84. The method according to any of the previous embodiments, wherein the digital 3D representations of the upper and lower wax rims are virtually brought into occlusion, and where the position and orientation of the occlusal plane is determined therefrom.

85. The method according to any of the previous embodiments, wherein the digital 3D representations of the upper and lower wax rims are virtually arranged in relation to the digital 3D representation of the patient's mandibular and maxillary gums such that the combined gum-wax rim model is generated.

86. The method according to any of the previous embodiments, wherein the lip line of the denture is derived from the combined gum-wax rim model.

87. The method according to any of the previous embodiments, wherein the incisal edge of the anterior teeth of the mandibular denture is derived from the combined gum-wax rim model.

88. The method according to any of the previous embodiments, wherein the occlusal plane is derived from the combined gum-wax rim model.

89. The method according to any of the previous embodiments, wherein the incisal edge of the anterior teeth of the maxillary denture is derived from the combined gum-wax rim model.

90. The method according to any of the previous embodiments, wherein the occlusion or occlusal plane of the patient's mouth is derived from the upper and lower wax rims.

91. The method according to any of the previous embodiments, wherein the shape of the patient's lips is derived from the upper and lower wax rims.

92. The method according to any of the previous embodiments, wherein the teeth models is virtually snapped to the inside of the digital 3D representation(s) of the wax rim(s) for ensuring that there is sufficient space for the teeth behind the patient's lips.

93. The method according to any of the previous embodiments, wherein the virtual teeth models are virtually arranged in relation to the digital 3D representation of the patient's gum based on a visualization of the virtual teeth models relative to said combined gum-wax rim model.

94. The method according to any of the previous embodiments, wherein virtually arranging the virtual teeth models in relation to the digital 3D representation of the patient's gum comprises rotating and/or translating the virtual teeth models with respect to the digital 3D representation of the patient's gum.

95. The method according to any of the previous embodiments, wherein the method comprises virtually arranging at least the teeth part of the denture in relation to a virtual articulator and performing a dynamic virtual articulation to evaluate the occlusion of the denture.

96. The method according to any of the previous embodiments, wherein the denture teeth are pre-manufactured teeth, such as pre-manufactured acrylic teeth.

97. The method according to any of the previous embodiments, wherein the method comprises determining a target form of the denture teeth.

98. The method according to any of the previous embodiments, wherein the method comprises:
  performing virtual articulation of the denture, and
  virtually removing a part of one or more of the teeth models, if the virtual articulation indicates that removal is suitable.

99. The method according to any of the previous embodiments, wherein the method comprises:
  performing virtual articulation of the denture, and
  virtually adjusting the position and/or orientation of one or more of the teeth models, if the virtual articulation indicates that adjustment is suitable.

100. The method according to any of the previous embodiments, wherein the virtual teeth models correspond to exact versions the denture teeth.

101. The method according to any of the previous embodiments, wherein the method comprises adjusting the size, shape, length, width, or thickness of the pre-manufactured teeth to obtain said target form.

102. The method according to any of the previous embodiments, wherein the denture teeth are customized teeth which are represented by CAD teeth models.

103. The method according to any of the previous embodiments, wherein the CAD teeth models of the denture teeth are modified with respect to their size, shape, length, width, distribution of mass, or thickness to obtain said target form.

104. The method according to any of the previous embodiments, wherein the digital 3D representation of the patient's gum is obtained by scanning the patient's gingival using an intraoral scanner.

105. The method according to any of the previous embodiments, wherein the digital 3D representation of the patient's gum is obtained by scanning at least part of an impression of the patient's gum and/or by scanning at least part of a physical model of the patient's gum.

106 The method according to any of the previous embodiments, wherein the method is for modeling a maxillary and/or a mandibular denture.

107. The method according to any of the previous embodiments, wherein at least the teeth part of a maxillary and the teeth part of a mandibular denture are modeled simultaneously.

108. The method according to any of the previous embodiments, wherein at least part of the method is computer-implemented.

109. The method according to any of the previous embodiments, wherein the extent of undercut sections between the denture and the gums is controlled.

110. The method according to any of the previous embodiments, wherein the method comprises performing a partial wax block-out of undercuts.

111. The method according to any of the previous embodiments, wherein the method comprises mirroring of teeth.

112. The method according to any of the previous embodiments, wherein the mirroring of teeth is such that the arrangement of denture teeth on one side of an arch is determined by mirroring the arrangement of the denture teeth on the opposite side of the arch.

113. The method according to any of the previous embodiments, wherein the mirroring of teeth is such that the shape of the denture teeth on one side of an arch is determined by mirroring the shape of the denture teeth on the opposite side of the arch.

114. The method according to any of the previous embodiments, wherein the result of the modeling of the digital denture designs is a virtual model of the denture which is completely ready for efficient output on a variety of milling machines or 3D printers.

115. The method according to any of the previous embodiments, wherein the method comprises virtually arranging one or more implants relative to the virtual teeth models and the gingival part of the denture.

116. The method according to any of the previous embodiments, wherein the method comprises virtually connecting one or more of the virtual teeth models and/or the gingival part of the denture to the one or more implants.

117. The method according to any of the previous embodiments, wherein the method comprises virtually cutting back or offsetting the virtual teeth models.

118. The method according to any of the previous embodiments, wherein a veneering layer may be virtually designed on virtually cut backed or offsetted teeth.

119. The method according to any of the previous embodiments, wherein the virtual model teeth are configured for being virtually reduced in size.

120. The method according to any of the previous embodiments, wherein the method comprises virtually arranging a 2D image of the patient's lips relative to the digital design of the denture.

121. The method according to any of the previous embodiments, wherein the method comprises virtually arranging and aligning a 2D image of the patient's lips relative to the digital 3D representations of the wax rims.

122. The method according to any of the previous embodiments, wherein the method comprises defining the thickness of the gingival part of the denture.

123. A method for manufacturing a denture for a patient, where the denture comprises a gingival part and denture teeth, wherein the method comprises:
obtaining a digital denture design, where the digital denture design is modeled using the method according to any of embodiments 1-122;
manufacturing at least part of the denture by means of computer aided manufacturing (CAM).

The invention claimed is:

1. A method for modeling a digital design of a denture for a patient, said denture comprising a gingival part and a teeth part comprising a set of denture teeth, where the method comprises:
obtaining a digital 3D representation of the patient's gum;
obtaining a digital 3D representation of a lower wax rim or obtaining a digital 3D representation of an upper wax rim;
combining the digital 3D representation of the patient's gum with the digital 3D representation of the lower wax rim or the digital 3D representation of the upper wax rim to form a combined gum-wax rim model which represents the space available for the denture teeth and the gingival part;
obtaining virtual teeth models corresponding to the denture teeth;
arranging the teeth models relative to the combined gum-wax rim model; and
generating a virtual outer gingival surface of the gingival part of the denture.

2. The method according to claim 1, wherein the method comprises providing a straight occlusal plate or a curved occlusal plate.

3. The method according to claim 1, wherein the method comprises forming an upper wax rim for the patient's maxillary arch and forming a lower wax rim for the patient's mandibular arch.

4. The method according to claim 3, wherein the method comprises obtaining a digital 3D representation of the lower wax rim and obtaining a digital 3D representation of the upper wax rim.

5. The method according to claim 4, wherein the method comprises:
combining the digital 3D representation of the patient's gum with the digital 3D representation of the lower wax rim and the digital 3D representation of the upper wax rim to form an upper combined gum-wax rim model and a lower combined gum-wax rim model which represent the space available for the denture teeth and the gingival part; and
arranging the teeth models relative to the digital 3D representations of the upper wax rim model and the lower wax rim model.

6. The method according to claim 3, wherein the method comprises arranging physical models of the patient's mandibular arch and the patient's maxillary arch and the lower and upper wax rims in a stack according to their relative positions in occlusion, and obtaining a digital 3D representation of this stack.

7. The method according to claim 6, wherein the method comprises virtually aligning the digital 3D representations of the patient's mandibular and maxillary gums and the digital 3D representation of the stack such that a combined gum-wax rim model is generated.

8. The method according to claim 3, wherein the digital 3D representations of the upper and lower wax rims are virtually brought into occlusion, and where the position and orientation of the occlusal plane is determined therefrom.

9. The method according to claim 3, wherein the digital 3D representations of the upper and lower wax rims are virtually arranged in relation to the digital 3D representation of the patient's mandibular and maxillary gums such that the combined gum-wax rim model is generated.

10. The method according to claim 1, wherein the method comprises providing a virtual occlusal plate relative to the digital 3D representations of the upper or lower wax rim and/or the digital 3D representation of the patient's gum, and virtually arranging the virtual teeth models relative to the virtual occlusal plate.

11. The method according to claim 1, wherein the virtual teeth models in a lower jaw or an upper jaw are arranged in occlusion by means of a virtual occlusal plate, and the virtual teeth models are then arranged in the upper jaw or lower jaw, respectively, relative to already arranged teeth models in an antagonist jaw.

12. The method according to claim 1, wherein the virtual teeth models are virtually snapped to an occlusal plate of the denture.

13. The method according to claim 1, wherein interproximal contact between neighbor teeth models is maintained, when a position, shape and/or orientation of one or more of the teeth models is adjusted.

14. The method according to claim 1, wherein the method comprises virtually adjusting the position, shape and/or orientation for a group of teeth models.

15. The method according to claim 1, wherein the method comprises providing a number of characteristic points on the digital 3D representation of the lower jaw and/or on the digital 3D representation of the upper jaw.

16. The method according to claim 15, where the characteristic points determine the placement of teeth models on the jaw(s).

17. The method according to claim 16, wherein the virtual teeth models are selected from a virtual library of teeth models based on relative positions of the characteristic points.

18. The method according to claim 1, wherein the method comprises defining a gingival 3D spline in relation to the digital 3D representation of the patient's gum.

19. The method according to claim 18, wherein the virtual outer gingival surface is configured for connecting the gingival 3D spline and the virtual teeth models.

20. The method according to claim 1, wherein gingival-tooth lines are defined for said virtual teeth models, and wherein the method comprises connecting the virtual outer gingival surface to the gingival-tooth lines on the virtual teeth models.

21. The method according to claim 1, wherein the teeth models are virtually snapped to the digital 3D representation of the wax rim.

22. The method according to claim 1, wherein the occlusal plane is derived from the combined gum-wax rim model.

23. The method according to claim 1, wherein the teeth models are virtually snapped to the inside of the digital 3D representation(s) of the wax rim for ensuring that there is sufficient space for the teeth behind the patient's lips.

24. The method according to claim 1, wherein arranging the teeth models relative to the digital 3D representation of the combined gum-wax rim model includes arranging the teeth models inside of the combined lower gum-wax rim or the combined upper gum-wax rim.

25. The method according to claim 1, wherein arranging the teeth models relative to the combined gum-wax rim model comprises virtually overlaying the teeth models on the combined gum-wax rim model.

* * * * *